US009260519B2

(12) United States Patent
Gujral et al.

(10) Patent No.: US 9,260,519 B2
(45) Date of Patent: Feb. 16, 2016

(54) FRIZZLED 2 AS A TARGET FOR THERAPEUTIC ANTIBODIES IN THE TREATMENT OF CANCER

(75) Inventors: Taranjit S. Gujral, Brookline, MA (US); Gavin MacBeath, Wakefield, MA (US)

(73) Assignee: PRESIDENT AND FELLOWS OF HARVARD COLLEGE, Cambridge, MA (US)

( * ) Notice: Subject to any disclaimer, the term of this patent is extended or adjusted under 35 U.S.C. 154(b) by 49 days.

(21) Appl. No.: 14/127,017

(22) PCT Filed: Jun. 15, 2012

(86) PCT No.: PCT/US2012/042770
§ 371 (c)(1),
(2), (4) Date: May 13, 2014

(87) PCT Pub. No.: WO2012/174446
PCT Pub. Date: Dec. 20, 2012

(65) Prior Publication Data
US 2014/0242070 A1   Aug. 28, 2014

Related U.S. Application Data

(60) Provisional application No. 61/498,353, filed on Jun. 17, 2011.

(51) Int. Cl.
*A61K 39/395* (2006.01)
*C07K 16/28* (2006.01)
*C07K 16/30* (2006.01)
*A61K 39/00* (2006.01)

(52) U.S. Cl.
CPC ............ *C07K 16/28* (2013.01); *C07K 16/2863* (2013.01); *C07K 16/30* (2013.01); *A61K 2039/505* (2013.01); *C07K 2317/34* (2013.01); *C07K 2317/73* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 7,250,496 | B2 | 7/2007 | Bentwich |
| 7,361,336 | B1 | 4/2008 | Bergstein |
| 7,413,873 | B2 | 8/2008 | Waterman et al. |
| 7,572,640 | B2 | 8/2009 | Goix et al. |
| 7,659,116 | B2 | 2/2010 | Buehring et al. |
| 7,713,526 | B2 | 5/2010 | Rhee et al. |
| 7,723,055 | B2 | 5/2010 | Jones et al. |
| 7,723,477 | B2 | 5/2010 | Gurney et al. |
| 7,754,221 | B2 | 7/2010 | Szalay et al. |
| 7,825,099 | B2 | 11/2010 | Feinstein |
| 7,855,279 | B2 | 12/2010 | Schellenberger et al. |
| 7,867,705 | B2 | 1/2011 | Wands et al. |
| 7,939,263 | B2 | 5/2011 | Clarke et al. |
| 7,959,923 | B2 | 6/2011 | You et al. |
| 7,982,013 | B2 | 7/2011 | Gurney et al. |
| 8,158,761 | B2 | 4/2012 | Wands et al. |
| 8,188,231 | B2 | 5/2012 | Lazar et al. |
| 8,221,751 | B2 | 7/2012 | Nakamura et al. |
| 8,507,442 | B2 * | 8/2013 | Gurney et al. ............... 514/19.3 |
| 8,551,789 | B2 * | 10/2013 | Gurney ........................ 436/501 |
| 2002/0187502 | A1 | 12/2002 | Waterman et al. |
| 2003/0044409 | A1 * | 3/2003 | Carson et al. ............... 424/143.1 |
| 2003/0165500 | A1 | 9/2003 | Rhee et al. |
| 2004/0224887 | A1 | 11/2004 | Jessel et al. |
| 2004/0247593 | A1 | 12/2004 | He et al. |
| 2005/0130199 | A1 | 6/2005 | Carson et al. |
| 2006/0019256 | A1 | 1/2006 | Clarke et al. |
| 2006/0019320 | A1 | 1/2006 | Civenni et al. |
| 2007/0036740 | A1 | 2/2007 | Reed |
| 2007/0116701 | A1 | 5/2007 | Gurney et al. |
| 2007/0185024 | A1 | 8/2007 | Jessell et al. |
| 2007/0219257 | A1 | 9/2007 | Beachy et al. |
| 2008/0038272 | A1 | 2/2008 | Buehring et al. |
| 2008/0267951 | A1 | 10/2008 | You et al. |
| 2008/0292546 | A1 | 11/2008 | Clarke et al. |
| 2008/0299135 | A1 | 12/2008 | Zou |

(Continued)

FOREIGN PATENT DOCUMENTS

| EP | 1648506 B1 | 2/2012 |
| JP | 2004051557 A | 2/2004 |
| WO | 02/092635 A2 | 11/2002 |
| WO | 03/004045 A2 | 1/2003 |
| WO | 2004/020668 A2 | 3/2004 |

(Continued)

OTHER PUBLICATIONS

Strome et al., The Oncologist, 2007; 12:1084-95.*
Brand et al., Anticancer Res. 2006; 26:463-70.*
Hanaki et al., Mol.Cancer Ther. 11(2): 298-307 (2012) "An anti-Wnt5a antibody suppresses metastasis of gastric cancer cells in vivo by inhibiting receptor-mediated endocytosis."

(Continued)

*Primary Examiner* — Sheela J Huff
(74) *Attorney, Agent, or Firm* — Nixon Peabody LLP; David S. Resnick; Shayne Y. Huff

(57) ABSTRACT

Disclosed herein are methods of treating cancer in a subject, and methods for inhibiting growth, migration and/or invasion of a cancer cell in the subject, comprising administering to the subject a therapeutically effective amount of an antibody or antigen binding fragment thereof that downmodulates Fzd2. The antibody may specifically bind Fzd2, and may promote internalization of the Fzd2 receptor by the cancer cells and/or prevent ligand binding to Fzd2. Specific antibodies, and also specific portions of the Fzd2 molecule for antibody binding are disclosed. In one embodiment the antibody specifically binds to the epitope HGAEQICVGQNHSEDGAPAL (SEQ ID NO: 1). Specific cancers (e.g. late stage hepatocellular carcinoma), intended for treatment are provided, and include cancers that exhibit overexpression of Fzd2, and/or Wnt5a.

24 Claims, 23 Drawing Sheets

(56) References Cited

U.S. PATENT DOCUMENTS

| | | | |
|---|---|---|---|
| 2010/0068708 A1 | 3/2010 | Hood et al. |
| 2010/0104574 A1 | 4/2010 | Gurney et al. |
| 2011/0020368 A1 | 1/2011 | Hynes |
| 2011/0123532 A1 | 5/2011 | Gurney et al. |
| 2011/0224243 A1 | 9/2011 | Rethore |
| 2011/0305695 A1 | 12/2011 | Satyal et al. |
| 2011/0318341 A1 | 12/2011 | Gurney et al. |
| 2014/0017253 A1 | 1/2014 | Gurney et al. |

FOREIGN PATENT DOCUMENTS

| | | |
|---|---|---|
| WO | 2004/026908 A1 | 4/2004 |
| WO | 2004/042028 A2 | 5/2004 |
| WO | 2005/005601 A2 | 1/2005 |
| WO | 2005/017109 A2 | 2/2005 |
| WO | 2006/070432 A2 | 7/2006 |
| WO | 2007053577 A2 | 5/2007 |
| WO | 2008/031009 A2 | 3/2008 |
| WO | 2010/037041 A2 | 4/2010 |
| WO | 2010/078458 A1 | 7/2010 |
| WO | 2011/004379 A1 | 1/2011 |
| WO | 2011/088127 A1 | 7/2011 |
| WO | 2013/086260 A2 | 6/2013 |
| WO | 2013/130364 A1 | 9/2013 |

OTHER PUBLICATIONS

Apte et al., "Wnt/B-Catenin Signaling Mediates Oval Cell Response in Rodents", Hepatology, 47(1): 288-295 (2008).

He et al., "A Member of the Frizzled Protein Family Mediating Axis Induction by Wnt-5a", Science, 275: 1652-1654 (1997).

Iozzo et al., "Aberrant Expression of the Growth Factor Wnt-5A in Human Malignancy", Cancer Research 55: 3495-3499 (1995).

Kawakami et al., "WNT Signals Control FGF0Dependent Limb Initiation and AER Induction in the Chick Embryo", Cell, 104: 891-900 (2001).

Kamino et al., "Wnt-5a signaling is correlated with infiltrative activity in human glioma by inducing cellular migration and MMP-2", Cancer Science, 102(3): 540-548 (2011).

Kuhl et al., "CA2/Calmodulin-dependent Protein Kinase II Is Stimulated by Wnt and Frizzled Homologs and Promotes Ventral Cell Fates in Xenopus", J Biol Chem, 275(15): 12701-12711 (2000).

Kuhl et al., "Antagonistic regulation of convergent extension movements in Xenopus by Wnt/B-catenin and Wnt/Ca2 signaling", Mech Dev, 106: 61-76 (2001).

Lee et al., "Wnt/frizzled signaling in hepatocellular carcinoma", Front Biosci, 11: 1901-1915 (2006).

Lejeune et al., "Wnt5a Cloning, Expression, and Up-Regulation in Human Primary Breast Cancers", Clin Cancer Res, 1: 215-222 (1995).

Reya et al., "Wnt signalling in stem cells and cancer", Nature, 434: 843-850 (2005).

Slusarski et al., "Modulation of Embryonic Intracellular Ca2 Signaling by Wnt-5A", Dev Biol, 118: 114-120 (1997).

Toyofuku et al., "Wnt/frizzled-2 Signaling Induces Aggregation and Adhesion among Cardiac Myocytes by Increased Cadherin-B-Catenin Complex", J Cell Biol, 150(1): 225-241 (2000).

Wang et al., "A Large Family of Putative Transmembrane Receptors Homologous to the Product of the Drosophila Tissue Polarity Gene frizzled", J Biol Chem, 271(8): 4468-4476 (1996).

Weeraratna et al., "Wnt5a signaling directly affects cell motility and invasion of metastatic melanoma", Cancer Cell, 1: 279-288 (2002).

Zeng et al., "Aberrant Wnt/B-Catenin Signaling in Pancreatic Adenocarcinoma", Neoplasia, 8(4): 279-289 (2006).

\* cited by examiner

```
         10         20         30         40         50         60
MRPRSALPRL LLPLLLLPAA GPAQFHGEKG ISIPDHGFCQ PISIPLCTDI AYNQTIMPNL 70         80         90        100        110        120
LGHTNQEDAG LEVHQFYPLV KVQCSPELRF FLCSMYAPVC TVLEQAIPPC RSICERARQG 130        140        150        160        170        180
CEALMNKFGF QWPERLRCEH FPRHGAEQIC VGQNHSEDGA PALLTTAPPP GLQPGAGGTP 190        200        210        220        230        240
GGPGGGGAPP RYATLEHPFH CPRVLKVPSY LSYKFLGERD CAAPCEPARP DGSMFFSQEE 250        260        270        280        290        300
TRFARLWILT WSVLCCASTF FTVTTYLVDM QRFRYPERPI IFLSGCYTMV SVAYIAGFVL 310        320        330        340        350        360
QERVVCNERF SEDGYRTVVQ GTKKEGCTIL FMMLYFFSMA SSIWWVILSL TWFLAAGMKW 370        380        390        400        410        420
GHEAIEANSQ YFHLAAWAVP AVKTITILAM GQIDGDLLSG VCFVGLNSLD PLRGFVLAPL 430        440        450        460        470        480
FVYLFIGTSF LLAGFVSLFR IRTIMKHDGT KTEKLERLMV RIGVFSVLYT VPATIVIACY 490        500        510        520        530        540
FYEQAFREHW ERSWVSQHCK SLAIPCPAHY TPRMSPDFTV YMIKYLMTLI VGITSGFWIW 550        560
SGKTLHSWRK FYTRLTNSRH GETTV
```

*FIG. 7*

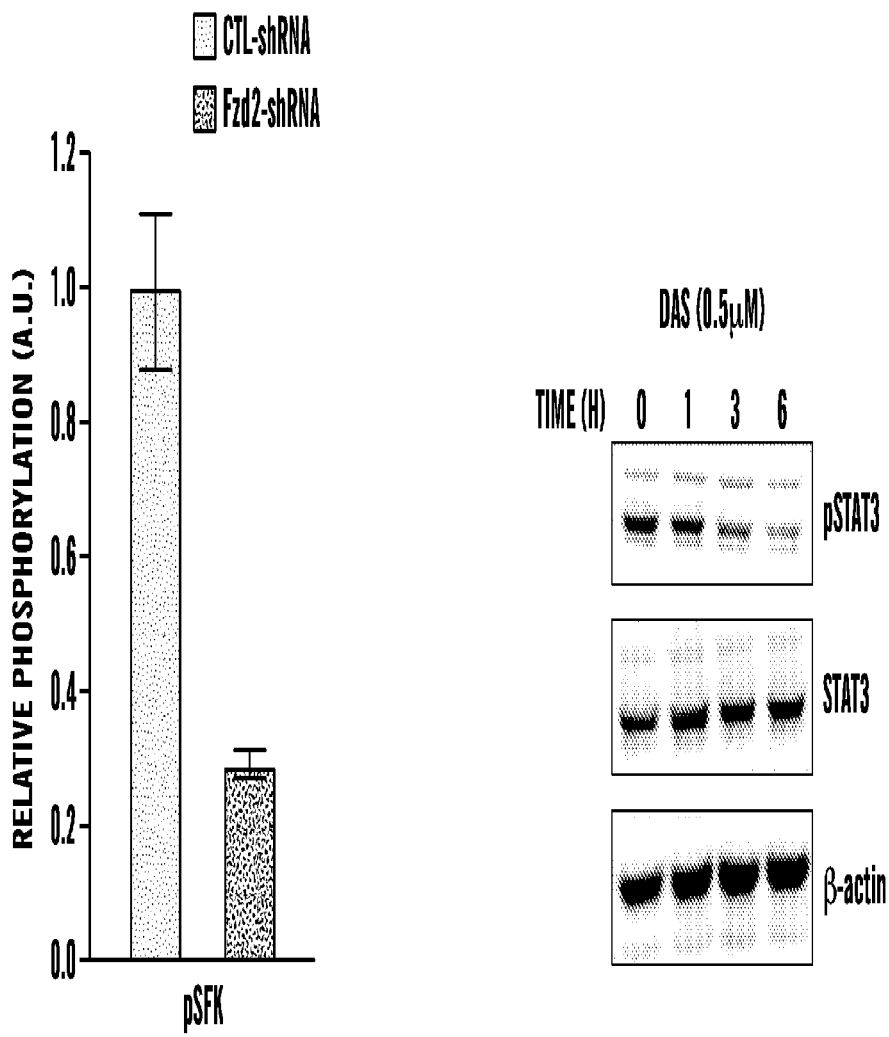
*FIG. 15A*  *FIG. 15B*

FRIZZLED 2 AS A TARGET FOR THERAPEUTIC ANTIBODIES IN THE TREATMENT OF CANCER

RELATED APPLICATIONS

This Application is a 35 U.S.C. 371 National Phase Entry Application of International Application No. PCT/US2012/042770 filed Jun. 15, 2012, which designates the U.S., and which claims the benefit under 35 U.S.C. §119(e) of U.S. Provisional Application Ser. No. 61/498,353, filed Jun. 17, 2011, the contents of each of which are incorporated herein by reference in their entirety.

GOVERNMENTAL SUPPORT

This invention was made with Government support under GM072872 awarded by the National Institutes of Health. The Government has certain rights in the invention.

SEQUENCE LISTING

The instant application contains a Sequence Listing which has been submitted in ASCII format via EFS-Web and is hereby incorporated by reference in its entirety. Said ASCII copy, created on Dec. 16, 2013, is named 002806-069422.txt and is 5,963 bytes in size.

FIELD OF THE INVENTION

The present invention relates to the field of cancer therapeutics.

BACKGROUND OF THE INVENTION

Liver cancer is the third most common cause of cancer mortality, with approximately 500,000 to 1 million annual deaths worldwide [1]. The American Cancer Society estimated that about 24,000 new cases of liver cancer occurred in the US in 2010, with more than 80% of these being hepatocellular carcinoma (HCC). An estimated 19,000 deaths in the US in 2010 resulted from liver cancer. The incidence and death rates for liver cancer have continued to increase since the early 1980s.

To date, surgical resection is considered the best treatment for liver cancer, but only a small proportion of patients qualify for surgery and there is a high rate of recurrence [2]. Many patients with HCC do not receive any therapy. Liver transplantation has been successful in treating limited-stage HCC. Only a minority of patients with HCC, however, qualifies for transplantation. Standard chemotherapy is poorly tolerated in patients who do not qualify for resection. Both doxorubicin and cisplatin are frequently used, but overall response rates are low, and neither prolongs survival substantially. The 5-year survival rate for patients with liver cancer is 14%. Five-year survival is 26% among patients in whom cancer is found at an early stage, compared to only 2% when it is found after spreading to distant organs. It is therefore critical to develop a better understanding of hepatocarcinogenesis at the molecular level to identify novel therapeutic targets that may play a pivotal role in the pathogenesis of this devastating disease.

HCC is the most common tumor that originates in the liver [2]. Recent studies have highlighted the role of various signaling pathways in liver carcinogenesis, including the Wnt/β-catenin pathway, Hedgehog signaling, and receptor tyrosine kinase-related pathways. These discoveries offer potential alternatives for novel targeted therapeutics. In particular, the role of Wnt signaling has been the subject of considerable interest in understanding the molecular pathogenesis of HCC [3]. Aberrant Wnt signaling has been implicated in many types of cancer, including cancers of the colon, skin, brain, liver and prostate[4]. In colorectal carcinomas, abnormal accumulation of β-catenin arises primarily as a result of mutations in β-catenin itself, as well as in APC and axin. These mutations are relatively rare in HCC, however, suggesting that misregulation of the Wnt pathway arises in other ways, including overexpression of other components of the pathway, such as Wnt ligands and Fzd receptors [3]. To date, however, it is not known which ligands or receptors are responsible for activation of the β-catenin pathway in HCC.

SUMMARY OF THE INVENTION

One aspect of the invention relates to a method of treating cancer in a subject comprising administering to the subject a therapeutically effective amount of an antibody or antigen binding fragment thereof that downmodulates Fzd2, such that the antibody or antigen binding fragment thereof is delivered to cancer cells of the subject, to thereby treat the cancer.

One aspect of the invention relates to a method of inhibiting growth, migration and/or invasion of a cancer cell in a subject comprising administering to the subject a therapeutically effective amount of an antibody or antigen binding fragment thereof, that downmodulates Fzd2, such that the antibody or antigen binding fragment thereof is delivered to the cancer cells, to thereby treat the cancer.

In one embodiment of the various methods described herein the antibody specifically binds Fzd2. In one embodiment of the various methods described herein the antibody binds to Fzd2 and promotes internalization of the Fzd2 receptor by the cancer cells. In one embodiment of the various methods described herein the antibody to Fzd2 prevents ligand binding to Fzd2. In one embodiment of the various methods described herein the antibody specifically binds an extracellular portion of the Fzd-2 protein. In one embodiment of the various methods described herein the antibody specifically binds to Fzd2 within a region of Fzd2 corresponding to amino acids 24-247 of Fzd2. In one embodiment of the various methods described herein the antibody specifically binds to Fzd2 within a region of Fzd2 corresponding to amino acids 125-163 of Fzd2. In one embodiment of the various methods described herein the antibody specifically binds to Fzd2 within a region of Fzd2 corresponding to amino acids 134-163 of Fzd2. In one embodiment of the various methods described herein the antibody specifically binds to Fzd2 within a region of Fzd2 corresponding to amino acids 144-163 of Fzd2. In one embodiment of the various methods described herein the antibody specifically binds to the epitope HGAEQICVGQNHSEDGAPAL (SEQ ID NO: 1).

In one embodiment of the various methods described herein the antibody is monoclonal. In one embodiment of the various methods described herein the antibody is polyclonal. In one embodiment of the various methods described herein the antibody is humanized.

In one embodiment of the various methods described herein the cancer is selected from the group consisting of gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer. In one embodiment of the various inventions described herein the cancer is liver cancer. In one embodiment of the various inventions described herein the cancer is late stage hepatocellular carcinoma. In one embodiment of the various methods described herein the cancer displays overexpression of Fzd2. In one embodiment of the various methods described herein the cancer displays overexpression of Wnt5a.

BRIEF DESCRIPTION OF THE DRAWINGS

FIG. 1A is a bar graph showing Fzd2 mRNA expression was significantly increased in late stages (Stage III and IV) of hepatocellular carcinoma compared with normal tissue (P<0.05). FIG. 1B is a bar graph showing the mRNA levels of Fzd2 expression correlated with tissue differentiation. Moderately and poorly differentiated tumors showed higher levels of Fzd2 compared with well differentiate tumor types.

FIG. 3A and FIG. 3B are bar graphs showing siRNA-mediated knockdown of Fzd2 or pre-treatment with anti-fzd2 antibody reduces cellular migration (FIG. 3A) and invasion (FIG. 3B) effects of Wnt5a at 2 hours.

FIG. 4A is a photograph of Western blots of biotinylated cell surface Fzd2 protein shows reduced protein levels upon Wnt5a or anti-Fzd2 pre-treatment. FIG. 4B is a bar graph showing relative quantitation of cell surface Fzd2 levels normalized for total Fzd2 in whole cell lysates.

FIG. 6A, left, is a schematic showing full length domain structure of Fzd2 protein. The domain structures of three fragments designed to map the epitope of anti-Fzd2 antibody are also shown. FIG. 6A, right, is a photograph of a Western blot showing anti-Fzd2 antibody can recognize only fragments 1 and 3. FIG. 6B, left, is a schematic showing the positions of overlapping residues in three peptides designed to map the epitope of anti-Fzd2 antibody. FIG. 6B, right, is a peptide array image showing anti-Fzd2 antibody recognizes only Peptide 2. Whole cell lysates from HEK293 cells overexpressing full length Fzd2 gene or empty vector (negative) were also printed on these arrays. CRD, cystein rich domain; TM, transmembrane.

FIG. 7 is the amino acid sequence of the human Fzd2 protein (SEQ ID NO: 2).

FIG. 8A, left, is a bar graph showing relative mRNA expression of five Fzd2-shRNA or control-shRNA expression FOCUS cells. FIG. 8A, right, is an image of western blots showing knockdown of Fzd2 protein levels. FIG. 8B is a graphical representation of data that shows knockdown of Fzd2 reduces FOCUS cell migration. Relative wound density of parental (wt) or Fzd2-shRNA or control-shRNA expressing FOCUS cells monitored for 60 h. FIG. 8C, left, is a bar graph of data showing FOCUS cells, in the presence of exogenous Wnt5a in the bottom of a Boyden chamber, treated with or without anti-fzd2 antibody reduces cellular migration at 2 h. FIG. 8C, right, is a bar graph of data showing FOCUS cells, in the presence of exogenous Wnt5a in the bottom of a Boyden chamber, treated with or without anti-fzd2 antibody reduces cellular invasion. FIG. 8D is a collection of data indicating anti-Fzd2 antibody causes internalization of cell surface Fzd2 receptors. FIG. 8D, left, are images of Western blots of biotinylated cell surface Fzd2 protein. Reduced protein levels were observed upon Wnt5a or anti-Fzd2 pre-treatment. FIG. 8D, right, is a bar graph showing relative quantitation of cell surface Fzd2 levels normalized for total Fzd2 in whole cell lysates. FIG. 8E and FIG. 8F are graphical representations of data that indicate Fzd2 knockdown reduces tumor growth in nude mice. FOCUS cells were injected s.c. into athymic mice and the ability of cells to form tumor outgrowths was monitored in the presence or absence of siRNA against Fzd2 (FIG. 8E) or Fzd2-shRNA (FIG. 8F).

FIG. 11A contains images of human cytokine array probed with conditioned media from FOCUS-WT (top) and FOCUS-shFzd2 (bottom). After detection, the array data were quantified to generate a protein profile. FIG. 11B is a bar graph showing abundance of 36 cytokines measured using this assay. The amount of SerpinE1 and siCAM1 released was significantly lower in the condition media from FOCUS-shFzd2 cells.

FIG. 14A is an image of an Immunoblot showing STAT3, ERK1/2, and MEK1/2 phosphorylation in wild-type FOCUS cells, and FOCUS cells with knockdown of Fzd2. Similar results were demonstrated in other late stage cell lines and with treatment with anti-Fzd2 antibody. FIG. 14B is a bar graph showing stat3 transcription activity using a reporter/luciferase-based assay in wild-type FOCUS and SNU449 cells, and cells knockdown with Fzd2 or STAT3. Similar results were demonstrated in other late stage cell lines and with treatment with anti-Fzd2 antibody. FIG. 14C is a collection of dose-response curves showing the effect of small molecule inhibitor against Stat3 on cell migration of late stage HCC cell lines (FOCUS).

FIG. 15A-FIG. 15C shows experimental results that indicate Fzd2 regulates the phosphorylation status of Src family kinases which phosphorylate Stat3 in late stage HCC cell lines. FIG. 15A is a bar graph showing phosphorylation of src family kinases in wild-type FOCUS cells, and FOCUS cells with knockdown of Fzd2. Similar results were demonstrated in other late stage cell lines. FIG. 15B is a photograph of experimental results that indicate the molecule inhibitor (dasatinib) against SFK abolishes stat3 phosphorylation in FOCUS cells. FIG. 15C is a collection of dose-response curves showing the effect of small molecule inhibitor against SFK on cell migration of late stage HCC cell lines (FOCUS).

DETAILED DESCRIPTION OF THE INVENTION

Figure 1A:
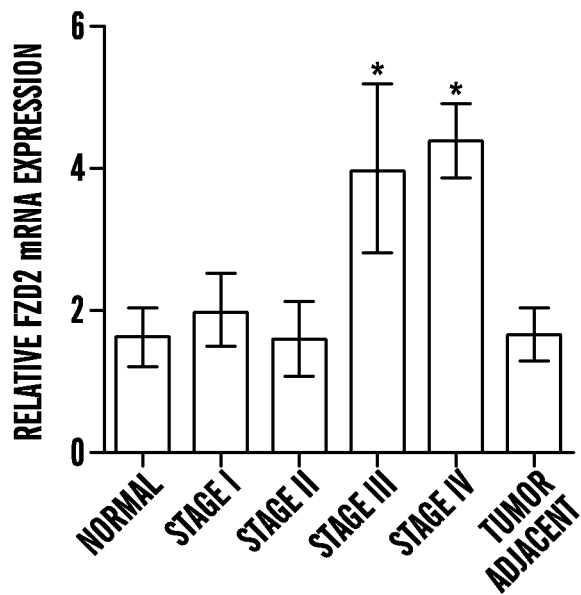
FIG. 1A-FIG. 1B show experimental results which indicate Fzd2 is overexpressed in late stage and poorly differentiated Hepatocellular carcinoma (HCC). 48 tissue samples obtained from patients with histopathologically confirmed HCC (stage I, n=7; stage II, n=8; stage III, n=8; stage IV, n=3; tumor lesion, n=14), as well as in normal liver samples (n=8).

Aspects of the invention relate to the finding that specific binding of the Frizzled 2 receptor (Fzd2) on hepatocellular carcinoma cells by an antibody reduces various tumorigenic properties of the cells. The antibody binding reduces the cell migration, the cell invasion, as well as growth of the cells. As such, one aspect of the invention relates to a method for inhibiting one or more tumorigenic properties of a tumor cell (e.g., growth, migration and/or invasiveness). The method comprises contacting the tumor cell with an effective amount of an agent that downmodulates Fzd2 in the cell (e.g. an antibody or antigen binding fragment thereof), to thereby downmodulate the Fzd2 in the cell. In one embodiment, the agent specifically downmodulates the Fzd2 in the cell, that is to say the agent does not downmodulate other closely related proteins (e.g., other Fzd proteins described herein). In one embodiment, the agent promotes sufficient internalization of the Fzd2 receptor by the cancer cells to inhibit one or more tumorigenic properties of the cell. In one embodiment, the agent prevents ligand (Wnt5a) binding to Fzd2.

The findings reported herein can be extrapolated to the treatment of a tumor (e.g., cancer) in a subject. As such, another aspect of the invention relates to a method of treating a tumor (e.g., a cancer) in a subject. The method comprises administering to the subject a therapeutically effective amount of an agent (e.g., an antibody or antigen binding fragment thereof) that downmodulates Fzd2. In one embodiment, the agent specifically downmodulates the Fzd2 in the cell. Administration is performed by a method that delivers an effective amount of the agent to a sufficient portion of the tumor cells of the subject to thereby produce therapeutic results. Effective treatment results in inhibition of one or more properties of the tumor cells, including growth, migration, and invasion, of the tumor cells in the subject. In one embodiment, the treatment is useful for inhibition of metastasis of the tumor cells in the subject.

The methods described herein are applicable to the treatment of tumors at various stages of disease progression, ranging from preliminary stages of disease to significantly advanced stages of disease. The advanced stage of disease wherein the tumor exhibits the properties of high growth rate, significant migration and invasiveness, is often signified by the detection of metastasis of the tumor cells to other locations or organs in the subject (e.g, lymph nodes, lungs, brain).

In one embodiment, one or more of the properties of loss of growth control, migration, and invasiveness are exhibited by the tumor.

It may be advantageous to determine the rate of the tumor cell targeted by the methods described herein prior to treatment. A reproducible, statistically significant amount as detected by standard means in the art is sufficient to indicate the presence of the one or more properties of the tumor cells described herein. The extent of each property (e.g., rate of growth and degree of migration and invasive properties) can further be measured by standard methods in the art. Such methods can be used to determine the state of the tumor cell with respect to these properties, following or in the course of treatment, to detect inhibition (reduction of the one or more properties) of the tumor cells by the treatment.

In one embodiment, one or more of the properties (growth, migration, invasion, and metastasis) are undetectable in the tumor cells of the subject. In such a situation, the method described herein may result in delay or prevention of onset of one or more of the properties.

Target Cell Types

The methods described herein are suitable for use on a variety of tumor cell types. The tumors may be primary tumors or may be secondary tumors. The tumors may originate from any cell or organ in a subject. In one embodiment, the tumor is an epithelial tumor. In one embodiment the tumor arises in the gastrointestinal tract, prostate, ovary, breast, cervix, central nervous system, peripheral nervous system, lung, kidney, retina, blood, skin, liver, pancreas, or the genital-urinary system (e.g., testes, bladder) of a subject.

The tumor may have progressed to the stage of cancer. In one embodiment, the cancer is gastrointestinal cancer, prostate cancer, ovarian cancer, breast cancer, head and neck cancer, lung cancer, lymphoma, non-small cell lung cancer, cancer of the nervous system, kidney cancer, retina cancer, skin cancer (e.g., basal cell carcinoma, squamous cell carcinoma, and melanoma), liver cancer, pancreatic cancer, genital-urinary cancer or bladder cancer. In one embodiment, the cancer cell is a carcinoma, sarcoma, lymphoma, germ cell tumor or blastoma. In one embodiment, the cancer is hepatocellular carcinoma.

The cancer can be in any possible stage of disease progression (e.g., stage 0, I, II, III, IV). In one embodiment, the cancer is late stage hepatocellular carcinoma. In one embodiment, the cancer has exhibited signs of metastasis.

In one embodiment, the tumor exhibits overexpression of Fzd2 and/or Wnt5a, as compared to an appropriate control cell or tissue. Overexpression refers to an increased amount or level of the protein. Such an increase is detected as an identified, reproducible, quantitative or qualitative increase in the physical presence of a target molecule or molecules (e.g., Fzd2 or Wnt5a). An increase that is considered relevant to the methods described herein is an increase by at least about 5%, about 10%, about 20%, about 30%, about 40%, about 50%, about 60%, about 70%, about 80%, about 90%, about 95%, about 99%, about 100% of the protein level in an appropriate control. Significantly higher increases above a 2 fold increase would also be relevant to the methods described herein. Additionally, overexpression of a target protein can be determined by analysis of the mRNA in the cell encoding the target protein. An increase that is considered relevant to the methods described herein is an increase by at least about 5%, about 10%, about 20%, about 30%, about 40%, about 50%, about 60%, about 70%, about 80%, about 90%, about 95%, about 99%, about 100% of the mRNA level in an appropriate control. Significantly higher increases above a 2 fold increase would also be relevant to the methods described herein.

An increased amount is determined by measuring (e.g., quantitative) the target molecule(s) in a target cell or tissue, to produce a determined amount, followed by comparison to a control amount obtained by measuring the target molecule(s) in an appropriate control cell or tissue, under normal or non-disease conditions. Measurement in the target cell or tissue and in the control cell or tissue is performed by as close to identical methods as possible under the given experimental conditions. An appropriate control cell can be determined by the skilled practitioner. For example, normal adjacent tissue of the same cell type is often used as a control.

Downmodulation of the Fzd2 protein that results from the methods described herein can be detected by a variety of means. Downmodulation resulting from decreased Fzd2 protein expression can be detected by quantitative measurement of the protein in a cell. Downmodulation resulting from reducing one or more protein functions (e.g., ligand binding) can be detected by analysis of that function (e.g., measuring the amount of bound ligand). In one embodiment, downmodulation results from increasing internalization of the Fzd2 receptor. In one embodiment, the internalization reduces the total amount of Fzd2 receptor on the cell surface. In one embodiment, the Fzd2 receptor on the surface of the cell is reduced by at least about 5%, about 10%, about 20%, about 30%, about 40%, about 50%, about 60%, about 70%, about 80%, about 90%, about 95%, about 99%, about 100% of the amount on an appropriate control cell.

Fzd Proteins

The terms "frizzled protein" or "frizzled receptor" refer to a family of mammalian proteins. The Frizzled family comprises at least 10 mammalian genes. Human Frizzled receptors include Fzd1, Fzd2, Fzd3, Fzd4, Fzd5, Fzd6, Fzd7, Fzd8, Fzd9 and Fzd10. The sequences of the different human Frizzled receptors are publically available. The mammalian frizzled proteins share a number of common structural motifs. The N terminus located at the extracellular membrane surface is followed by a signal sequence, a domain of 120 amino acids with an invariant pattern of 10 cysteine residues, and a highly divergent region of 40-100 largely variable hydrophilic amino acids. Putative hydrophobic segments form seven membrane-spanning helices linked by hydrophilic loops, ending with the C terminus located at the intracellular face of the membrane. The cysteine-rich domains (CRDs) and the transmembrane segments are strongly conserved, suggesting a working model in which an extracellular CRD is tethered by a variable linker region to a bundle of seven membrane-spanning-helices. Frizzled protein receptors are, therefore, involved in a dynamic model of transmembrane signal transduction analogous to G-protein-coupled receptors with amino-terminal ligand binding domains.

The amino acid sequence of human Fzd2 is set forth in FIG. 7. Amino acids 1-23 are the signal peptide. Extra cellular domains of Fzd2 are encompassed by amino acids 24-247, 301-327, 392-414, and 483-519.

Wnt5a

Wnt5a (wingless-related MMTV integration site 5a) is a member of a large family of cysteine-rich growth factors. Proteins in this family are highly conserved and naturally secreted. The Wnt5a protein binds to members of the Frizzled (Fzd) family of seven-transmembrane domain receptors on the cell surface, including Fzd2, and this triggers a series of intracellular events that ultimately regulate gene transcription. These intracellular events are grouped according to two known signaling pathways, the canonical Wnt/β-catenin pathway (He et al., Science 275:652-654, 1997; Toyofuku et al., J. Cell Biol. 150:225-41, 2000; Kawakami et al., Cell 104:891-900, 2001) and the Wnt/Ca++ pathway (Slusarski et al., Dev. Biol. 182:114-120, 1997; Kuhl et al., J. Biol. Chem. 275:12701-12711, 2000; and Kuhl et al., Mech. Dev. 106:61-76, 2001). Upregulation of gene expression of WNT5a has been observed in various human cancers (Lejeune et al., Clin. Cancer Res. 1:215-222, 1995; Tozzo et al., Cancer Res. 55:3495-3499, 1995) and WNT5a has recently been reported to facilitate cell invasion in human metastatic melanoma (Weeraratna et al., Cancer Cell 1:279-88, 2002). Determination of expression levels of Wnt5a in a cell, tissue or a specific cancer is described in detail in U.S. Pat. No. 7,723,055.

Agents for Downmodulation

In one embodiment, the agent for downmodulation is specific for Fzd2. Specific, as the term is used herein in reference to downmodulation of Fzd2, refers to an absence of significant downmodulation of other related proteins, such as other Frizzled proteins or receptors (e.g., Fzd1, or Fzd3-Fzd10). Agents that specifically downmodulate Fzd2, and do not significantly downmodulate other Fzd proteins can be generated by routine methods.

Agents for downmodulation, as described herein can be chemicals; small molecules; nucleic acid sequences; nucleic acid analogues; proteins; peptides; aptamers; antibodies; or fragments thereof. Many such agents are known in the art and can be used in the present invention. Other such agents can be identified or generated for use in the present invention.

Such an agent can take the form of any entity that is normally absent (exogenous) or present at lower levels that those provided to the cell(s). Agents such as chemicals; small molecules; nucleic acid sequences; nucleic acid analogues; proteins; peptides; aptamers; antibodies, or antigen binding fragments thereof, can be identified or generated for use to downmodulate the Fzd2.

Agents in the form of a protein and/or peptide or fragment thereof can be used to downmodulate Fzd2. Examples of useful proteins are mutated proteins, genetically engineered proteins, peptides, synthetic peptides, recombinant proteins, chimeric proteins, antibodies, midibodies, minibodies, triabodies, humanized proteins, humanized antibodies, chimeric antibodies, modified proteins and fragments thereof. Agents also include antibodies (polyclonal or monoclonal), neutralizing antibodies, antibody fragments, peptides, proteins, peptide-mimetics, aptamers, hormones, small molecules, carbohydrates or variants thereof that function to inactivate the nucleic acid and/or protein of the gene products identified herein, and those as yet unidentified. Inhibitory agents can also be a chemical, small molecule, chemical entity, nucleic acid sequences, nucleic acid analogues or protein or polypeptide or analogue or fragment thereof.

The agent may function directly in the form in which it is administered. Alternatively, the agent can be modified or utilized intracellularly to produce something which downmodulates the Fzd2, such as introduction of a nucleic acid sequence into the cell and its transcription resulting in the production of the nucleic acid and/or protein inhibitor of Fzd2 within the cell. The agent can be made from any chemical, entity or moiety, including without limitation synthetic and naturally-occurring non-proteinaceous entities. In certain embodiments the agent is a small molecule having a chemical moiety. For example, chemical moieties included unsubstituted or substituted alkyl, aromatic, or heterocyclyl moieties including macrolides, leptomycins and related natural products or analogues thereof. Agents can be known to have a desired activity and/or property, or can be selected from a library of diverse compounds.

Antibodies and Antibody Binding Fragments

Antibodies that bind an extracellular region of Fzd2 are particularly suited for use in the methods described herein. In one embodiment, the antibody specifically binds Fzd2, and does not appreciably bind related Fzd molecules. Antibodies that bind specifically to Fzd2 (e.g., the extracellular region), and do not significantly bind to other Fzd proteins can be generated or otherwise identified by routine methods. By way of example, epitopes that are specific to Fzd2 can be used to generate or identify antibodies or antigen binding fragments thereof, by the methods described herein. The location of such epitopes can be determined, for example, by comparison of the amino acid sequences of the Fzd2 protein, to the amino acid sequences of related Fzd family members, to thereby identify regions of dissimilarity. In one embodiment, the antibody binds an extracellular portion of the Fzd2 protein. Useful extracellular portions of the Fzd2 protein include, without limitation, a region of Fzd2 corresponding to amino acids 24-247, amino acids 125-163, amino acids 134-163, and amino acids 144-163. In one embodiment, the antibody or antigen binding fragment binds a fragment of Fzd2 comprising the amino acid sequence HGAEQICVGQNHSEDGAPAL (SEQ ID NO: 1). In one embodiment, the antibody or antigen binding fragment binds the epitope within the amino acid sequence HGAEQICVGQNHSEDGAPAL (SEQ ID NO: 1). In one embodiment, the antibody or antigen binding fragment binds a subset of the amino acids within the amino acid sequence HGAEQICVGQNHSEDGAPAL (SEQ ID NO: 1), when present in the context of the Fzd2 protein (e.g., having the amino acid sequence shown in FIG. 7). In one embodiment, the antibody or antigen binding fragment binds 19 or less consecutive amino acids of HGAEQICVGQNHSEDGAPAL (SEQ ID NO: 1), within the context of the wild type Fzd2 protein. In one embodiment, the antibody or antigen binding fragment binds 18 or less, 17 or less, 16 or less, 15 or less, 14 or less, 13 or less, 12 or less, 11 or less, 10 or less, 9 or less, 8 or less, 7 or less, 6 or less, 5 or less, 4 or less, 3 or less, or 2 or less consecutive amino acids of HGAEQICVGQNHSEDGAPAL (SEQ ID NO: 1), within the context of the wild type Fzd2 protein.

Antibodies which were generated to Fzd2 from non-human species are also expected to recognize human Fzd2 if generated to epitopes which lie in areas of amino acid identity (e.g., 100% identity) to human Fzd2.

Detection of specific binding of an antibody to a region or epitope of Fzd2 is exemplified herein. The ability of a region or epitope to competitively inhibit binding of the antibody to a longer region of Fzd2, or to full length Fzd2 can also be used to identify the region or epitope to which an antibody or antigen binding fragment binds.

In one embodiment, the antibody binds to Fzd2, wherein that binding promotes internalization of the Fzd2 receptor by the tumor cells. In one embodiment, binding of the antibody to Fzd2 prevents or otherwise significantly reduces binding of Fzd2 to endogenous ligand. One such ligand is Wnt5a.

An antibody used in the present invention can be of any one of the various immunoglobulin isotypes. An antigen binding fragment of an antibody described herein is also useful in the methods described herein, and includes, without limitation, the Fab, scFv, Fv, dAb, and Fd fragments. Preferred for human therapeutic use are high affinity murine, chimeric, human and humanized antibodies, and antigen binding fragments thereof, having potent in vivo activity.

Structurally, the simplest antibody (IgG) comprises four polypeptide chains, two heavy (H) chains and two light (L) chains inter-connected by disulphide bonds. The light chains exist in two distinct forms called kappa (κ) and lambda (λ). Each chain has a constant region (C) and a variable region (V). Each chain is organized into a series of domains. The light chains have two domains, corresponding to the C region and the other to the V region. The heavy chains have four domains, one corresponding to the V region and three domains (1, 2 and 3) in the C region. The antibody has two arms (each arm being a Fab region), each of which has a VL and a VH region associated with each other. It is this pair of V regions (VL and VH) that differ from one antibody to another (owing to amino acid sequence variations), and which together are responsible for recognizing the antigen and providing an antigen binding site (ABS). In even more detail, each V region is made up from three complementarity determining regions (CDR) separated by four framework regions (FR). The CDR's are the most variable part of the variable regions, and they perform the critical antigen binding function. The CDR regions are derived from many potential germ line sequences via a complex process involving recombination, mutation and selection.

Certain identifiable fragments of a whole antibody also retain the ability to bind antigen. Such binding fragments are (i) the Fab fragment consisting of the VL, VH, CL and CH1 domains; (ii) the Fd fragment consisting of the VH and CH1 domains; (iii) the Fv fragment consisting of the VL and VH domains of a single arm of an antibody, (iv) the dAb fragment (Ward, E. S. et al., Nature 341, 544-546 (1989) which consists of a VH domain; (v) isolated CDR regions; and (vi) F(ab')2 fragments, a bivalent fragment comprising two Fab fragments linked by a disulphide bridge at the hinge region.

Although the two domains of the Fv fragment are coded for by separate genes, it is possible to make a synthetic linker that enables them to be made as a single protein chain (known as single chain Fv (scFv); Bird, R. E. et al., Science 242, 423-426 (1988) Huston, J. S. et al., Proc. Natl. Acad. Sci., USA 85, 5879-5883 (1988)) by recombinant methods. These scFv fragments were assembled from genes from monoclonal antibodies that had been previously isolated. In this application, the applicants describe a process to assemble scFv fragments from VH and VL domains that are not part of an antibody that has been previously isolated.

Antibodies useful in the present invention can be in the form of polyclonal, monoclonal, chimeric, humanized, and recombinant antibodies. Antigen-binding fragments can be generated from an antibody by methods known to the skilled practitioner. Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies.

Antibodies provide high binding avidity and unique specificity to a wide range of target antigens and haptens. Monoclonal antibodies useful in the practice of the present invention include whole antibody and fragments thereof and are generated in accordance with conventional techniques, such as hybridoma synthesis, recombinant DNA techniques and protein synthesis.

Polyclonal antibodies, or fragments thereof, can be derived from any species.

Useful monoclonal antibodies and fragments can be derived from any species (including humans) or can be formed as chimeric proteins which employ sequences from more than one species. Human monoclonal antibodies or "humanized" murine antibody are also used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction the possibly of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv-phage library. Some examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

One limitation of scFv molecules is their monovalent interaction with target antigen. One of the easiest methods of improving the binding of a scFv to its target antigen is to increase its functional affinity through the creation of a multimer. Association of identical scFv molecules to form diabodies, triabodies and tetrabodies can comprise a number of identical Fv modules. These reagents are therefore multivalent, but monospecific. The association of two different scFv molecules, each comprising a VH and VL domain derived from different parent Ig will form a fully functional bispecific diabody. A unique application of bispecific scFvs is to bind two sites simultaneously on the same target molecule via two (adjacent) surface epitopes. These reagents gain a significant avidity advantage over a single scFv or Fab fragments. A number of multivalent scFv-based structures has been engineered, including for example, miniantibodies, dimeric miniantibodies, minibodies, (scFv)2, diabodies and triabodies. These molecules span a range of valence (two to four binding sites), size (50 to 120 kDa), flexibility and ease of production. Single chain Fv antibody fragments (scFvs) are predominantly monomeric when the VH and VL domains are joined by, polypeptide linkers of at least 12 residues. The monomer scFv is thermodynamically stable with linkers of 12 and 25 amino acids length under all conditions. The noncovalent diabody and triabody molecules are easy to engineer and are produced by shortening the peptide linker that connects the variable heavy and variable light chains of a single scFv molecule. The scFv dimers are joined by amphipathic helices that offer a high degree of flexibility and the miniantibody structure can be modified to create a dimeric bispecific (DiBi) miniantibody that contains two miniantibodies (four scFv molecules) connected via a double helix. Gene-fused or disulfide bonded scFv dimers provide an intermediate degree of flexibility and are generated by straightforward cloning techniques adding a C-terminal Gly4Cys sequence. scFv-CH3 minibodies are comprised of two scFv molecules joined to an IgG CH3 domain either directly (LD minibody) or via a very flexible hinge region (Flex minibody). With a molecular weight of approximately 80 kDa, these divalent constructs are capable of significant binding to antigens. The Flex minibody exhibits impressive tumor localization in mice. Bi- and tri-specific multimers can be formed by association of different scFv molecules. Increase in functional affinity can be reached when Fab or single chain Fv antibody fragments (scFv) fragments are complexed into dimers, trimers or larger aggregates. The most important advantage of multivalent scFvs over monovalent scFv and Fab fragments is the gain in functional binding affinity (avidity) to target antigens. High avidity requires that scFv multimers are capable of binding simultaneously to separate target antigens. The gain in functional affinity for scFv diabodies compared to scFv monomers is significant and is seen primarily in reduced off-rates, which result from multiple binding to two or more target antigens and to rebinding when one Fv dissociates. When such scFv molecules associate into multimers, they can be designed with either high avidity to a single target antigen or with multiple specificities to different target antigens. Multiple binding to antigens is dependent on correct alignment and orientation in the Fv modules. For full avidity in multivalent scFvs target, the antigen binding sites must point towards the same direction. If multiple binding is not sterically possible then apparent gains in functional affinity are likely to be due the effect of increased rebinding, which is dependent on diffusion rates and antigen concentration. Antibodies conjugated with moieties that improve their properties are also contemplated for the instant invention. For example, antibody conjugates with PEG that increases their half-life in vivo can be used for the present invention. Immune libraries are prepared by subjecting the genes encoding variable antibody fragments from the B lymphocytes of naive or immunized animals or patients to PCR amplification. Combinations of oligonucleotides which are specific for immunoglobulin genes or for the immunoglobulin gene families are used. Immunoglobulin germ line genes can be used to prepare semisynthetic antibody repertoires, with the complementarity-determining region of the variable fragments being amplified by PCR using degenerate primers. These single-pot libraries have the advantage that antibody fragments against a large number of antigens can be isolated from one single library. The phage-display technique can be used to increase the affinity of antibody fragments, with new libraries being prepared from already existing antibody fragments by random, codon-based or site-directed mutagenesis, by shuffling the chains of individual domains with those of fragments from naive repertoires or by using bacterial mutator strains.

In one embodiment, the antibody or antigen binding fragment thereof, is produced by a SCID-hu mouse, for example the model developed by Genpharm. In one embodiment, a type of high avidity binding molecule, termed peptabody, created by harnessing the effect of multivalent interaction is contemplated.

Human antibodies against Fzd2 can be produced from non-human transgenic mammals having transgenes encoding at least a segment of the human immunoglobulin locus. Usually, the endogenous immunoglobulin locus of such transgenic mammals is functionally inactivated. Preferably, the segment of the human immunoglobulin locus includes unrearranged sequences of heavy and light chain components. Both inactivation of endogenous immunoglobulin genes and introduction of exogenous immunoglobulin genes can be achieved by targeted homologous recombination, or by introduction of YAC chromosomes. The transgenic mammals resulting from this process are capable of functionally rearranging the immunoglobulin component sequences, and expressing a repertoire of antibodies of various isotypes encoded by human immunoglobulin genes, without expressing endogenous immunoglobulin genes. The production and properties of mammals having these properties are described in detail by, e.g., Lonberg et al., WO93/12227 (1993); U.S. Pat. No. 5,877,397, U.S. Pat. No. 5,874,299, U.S. Pat. No. 5,814,318, U.S. Pat. No. 5,789,650, U.S. Pat. No. 5,770,429, U.S. Pat. No. 5,661,016, U.S. Pat. No. 5,633,425, U.S. Pat. No. 5,625,126, U.S. Pat. No. 5,569,825, U.S. Pat. No. 5,545,806, Nature 148, 1547-1553 (1994), Nature Biotechnology 14, 826 (1996), Kucherlapati, WO 91/10741 (1991) (each of which is incorporated by reference in its entirety for all purposes). Transgenic mice are particularly suitable. Anti-Fzd2 antibodies are obtained by immunizing a transgenic nonhuman mammal, such as described by Lonberg or Kucherlapati, supra with Fzd2 or a fragment thereof. Monoclonal antibodies are prepared by, e.g., fusing B-cells from such mammals to suitable myeloma cell lines using conventional Kohler-Milstein technology. Human polyclonal antibodies can also be provided in the form of serum from humans immunized with an immunogenic agent Optionally, such polyclonal antibodies can be concentrated by affinity purification using Fzd2 or other Fzd2 peptide as an affinity reagent.

A further approach for obtaining human Fzd2 antibodies is to screen a DNA library from human B cells according to the general protocol outlined by Huse et al., Science 246:1275-1281 (1989). As described for trioma methodology, such B cells can be obtained from a human immunized with Fzd2, fragments, longer polypeptides containing Fzd2 or fragments or anti-idiotypic antibodies. Optionally, such B cells are obtained from a patient who is ultimately to receive antibody treatment. Antibodies binding to Fzd2 or a fragment thereof are selected. Sequences encoding such antibodies (or a binding fragments) are then cloned and amplified. The protocol described by Huse is rendered more efficient in combination with phage-display technology. See, e.g., Dower et al., WO 91/17271 and McCafferty et al., WO 92/01047, U.S. Pat. No. 5,877,218, U.S. Pat. No. 5,871,907, U.S. Pat. No. 5,858,657, U.S. Pat. No. 5,837,242, U.S. Pat. No. 5,733,743 and U.S. Pat. No. 5,565,332 (each of which is incorporated by reference in its entirety for all purposes). In these methods, libraries of phage are produced in which members display different antibodies on their outer surfaces. Antibodies are usually displayed as Fv or Fab fragments. Phage displaying antibodies with a desired specificity are selected by affinity enrichment to an Fzd2 peptide or fragment thereof.

In a variation of the phage-display method, human antibodies having the binding specificity of a selected murine antibody can be produced. See U.S. Pat. No. 6,172,197, issued Jan. 9, 2001. In this method, either the heavy or light chain variable region of the selected murine antibody is used as a starting material. If, for example, a light chain variable region is selected as the starting material, a phage library is constructed in which members display the same light chain variable region (i.e., the murine starting material) and a different heavy chain variable region. The heavy chain variable regions are obtained from a library of rearranged human heavy chain variable regions. A phage showing strong specific binding for Fzd2 (e.g., at least 108 and preferably at least 109 M-1) is selected. The human heavy chain variable region from this phage then serves as a starting material for constructing a further phage library. In this library, each phage displays the same heavy chain variable region (i.e., the region identified from the first display library) and a different light chain variable region. The light chain variable regions are obtained from a library of rearranged human variable light chain regions. Again, phage showing strong specific binding for Fzd2 are selected. These phage display the variable regions of completely human anti-Fzd2 antibodies. These antibodies usually have the same or similar epitope specificity as the murine starting material.

In one embodiment, the agent inhibits gene expression (i.e., suppress and/or repress the expression of a gene of interest (e.g., the Fzd2 gene)). Such agents are referred to in the art as "gene silencers" and are commonly known to those of ordinary skill in the art. Examples include, but are not limited to a nucleic acid sequence, (e.g., for an RNA, DNA, or nucleic acid analogue). These can be single or double stranded. They can encode a protein of interest, can be an oligonucleotide, a nucleic acid analogue. Included in the term "nucleic acid sequences" are general and/or specific inhibitors. Some known nucleic acid analogs are peptide nucleic acid (PNA), pseudo-complementary PNA (pc-PNA), locked nucleic acids (LNA) and derivatives thereof. Nucleic acid sequence agents can also be nucleic acid sequences encoding proteins that act as transcriptional repressors, antisense molecules, ribozymes, small inhibitory nucleic acid sequences (e.g., RNAi, shRNAi, siRNA, micro RNAi (miRNA), and antisense oligonucleotides. Many such molecules for inhibiting Fzd2 are known in the art. As such these inhibitors can function as an agent in the present invention.

One type of downmodulatory agent for use in the present invention is an RNAi molecule (e.g., an siRNA or miRNA). The term "RNAi" and "RNA interfering" with respect to an agent of the invention are used interchangeably herein. The term "RNAi" as used herein refers to interfering RNA or RNA interference, which is a means of selective post-transcriptional gene silencing by destruction of specific mRNA by molecules that bind and inhibit the processing of mRNA, for example inhibit mRNA translation or result in mRNA degradation. As used herein, the term "RNAi" refers to any type of interfering RNA, including but are not limited to, siRNAi, shRNAi, endogenous microRNA and artificial microRNA. For instance, it includes sequences previously identified as siRNA, regardless of the mechanism of down-stream processing of the RNA (i.e. although siRNAs are believed to have a specific method of in vivo processing resulting in the cleavage of mRNA, such sequences can be incorporated into the vectors in the context of the flanking sequences described herein).

RNAi molecules are typically comprised of a sequence of nucleic acids or nucleic acid analogs, specific for a target gene. A nucleic acid sequence can be RNA or DNA, and can be single or double stranded, and can be selected from a group comprising; nucleic acid encoding a protein of interest, oligonucleotides, nucleic acid analogues, for example peptide-nucleic acid (PNA), pseudo-complementary PNA (pc-PNA), locked nucleic acid (LNA).

As used herein an "siRNA" refers to a nucleic acid that forms a double stranded RNA, which double stranded RNA has the ability to reduce or inhibit expression of a gene or target gene when the siRNA is present or expressed in the same cell as the target gene, for example an HDF gene. The double stranded RNA siRNA can be formed by the complementary strands. In one embodiment, a siRNA refers to a nucleic acid that can form a double stranded siRNA. The sequence of the siRNA can correspond to the full length target gene, or a subsequence thereof. Typically, the siRNA is at least about 15-50 nucleotides in length (e.g., each complementary sequence of the double stranded siRNA is about 15-50 nucleotides in length, and the double stranded siRNA is about 15-50 base pairs in length, preferably about 19-30 base nucleotides, preferably about 20-25 nucleotides in length, e.g., 20, 21, 22, 23, 24, 25, 26, 27, 28, 29, or 30 nucleotides in length). An siRNA can be chemically synthesized, it can be produced by in vitro transcription, or it can be produced within a cell specifically utilized for such production.

In one embodiment, the siRNA is designed for inhibition of expression of Fzd2. Examples of such siRNA and methods of use to inhibit expression are known in the art (Published Patent Application WO 2010/039679; Truong et al., Genes & Dev. 20: 3185-3197 (2006); Barbieri et al., Cancer Res 65:2314-2320 (2005); Yuan et al., BMC Cancer 11:57 (2011); Yang et al. Cancer Res 71:3688-3700 (2011)). Examples of useful siRNA sequences for inhibiting Fzd2 are provided herein.

In one embodiment, use of the agent is to thereby result in a decrease in the target Fzd2 mRNA level in a cell by at least about 5%, about 10%, about 20%, about 30%, about 40%, about 50%, about 60%, about 70%, about 80%, about 90%, about 95%, about 99%, about 100% of the mRNA level typically measured in the cell in the absence of the RNAi. In one embodiment, the mRNA levels are decreased by at least about 70%, about 80%, about 90%, about 95%, about 99%, or about 100%.

The agent that is a nucleic acid to be expressed in the target cell may comprise a vector. Many such vectors useful for transferring exogenous genes into target mammalian cells are available. The vectors may be episomal, e.g., plasmids, virus derived vectors such cytomegalovirus, adenovirus, etc., or may be integrated into the target cell genome, through homologous recombination or random integration, e.g., retrovirus derived vectors such MMLV, HIV-1, ALV, etc. For modification of stem cells, lentiviral vectors are preferred. Lentiviral vectors such as those based on HIV or FIV gag sequences can be used to transfect non-dividing cells, such as the resting phase of human stem cells (see Uchida et al. (1998) P.N.A.S. 95(20): 11939-44). As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors".

Delivery of Agents to the Cell

The agent is contacted to the cell such that it can exert its intended effect on the cell. In one embodiment, the agent exerts its effects on the cells merely by interacting with the exterior of the cell (e.g., by binding to a receptor, such as with an antibody or antigen binding fragment). Agents that act on the cell internally (e.g., RNAi) may be delivered in a form that is readily taken up by the cell when contacted to the cell (e.g., in a formulation which facilitates cellular uptake and delivery to the appropriate subcellular location). In one embodiment, the agent is in a formulation in which it is readily taken up by the cell so that it can exert it effect.

Colloidal dispersion systems may be used as delivery vehicles and to enhance the in vivo stability of the agent to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 1995, 6, 698-708). Other examples of cellular uptake or membrane-disruption moieties include polyamines, e.g. spermidine or spermine groups, or polylysines; lipids and lipophilic groups; polymyxin or polymyxin-derived peptides; octapeptin; membrane pore-forming peptides; ionophores; protamine; aminoglycosides; polyenes; and the like. Other potentially useful functional groups include intercalating agents; radical generators; alkylating agents; detectable labels; chelators; or the like.

Other colloidal dispersion systems lipid particle or vesicle, such as a liposome or microcrystal, may be suitable for administration. The particles may be of any suitable structure, such as unilamellar or plurilamellar, so long as the antisense oligonucleotide is contained therein. Positively charged lipids such as N-[I-(2,3dioleoyloxi)propyll-N,N,N-trimethyl-anunoniummethylsulfate, or "DOTAP," are particularly preferred for such particles and vesicles. The preparation of such lipid particles is well known. See, e.g., U.S. Pat. Nos. 4,880, 635; 4,906,477; 4,911,928; 4,917,951; 4,920,016; and 4,921, 757, which are incorporated herein by reference. Other nontoxic lipid based vehicle components may likewise be utilized to facilitate uptake of the nucleic acid compound by the cell.

In some embodiments, in order to increase nuclease resistance in an RNAi agent as disclosed herein, one can incorporate non-phosphodiester backbone linkages, as for example methylphosphonate, phosphorothioate or phosphorodithioate linkages or mixtures thereof, into one or more non-RNASE H-activating regions of the RNAi agents. Such non-activating regions may additionally include 2'-substituents and can also include chirally selected backbone linkages in order to increase binding affinity and duplex stability. Other functional groups may also be joined to the oligonucleoside sequence to instill a variety of desirable properties, such as to enhance uptake of the oligonucleoside sequence through cellular membranes, to enhance stability or to enhance the formation of hybrids with the target nucleic acid, or to promote cross-linking with the target (as with a psoralen photo-cross-linking substituent). See, for example, PCT Publication No. WO 92/02532, which is incorporated herein in by reference.

Methods of delivering RNAi interfering (RNAi) agents, e.g., an siRNA, or vectors containing an RNA interfering agent, to the target cells (e.g., horizontal basal cells) can include, for example (i) injection of a composition containing the RNA interfering agent, e.g., an siRNA, or (ii) directly contacting the cell, with a composition comprising an RNA interfering agent, e.g., an siRNA. In another embodiment, RNA interfering agents, e.g., an siRNA can be injected directly into any blood vessel, such as vein, artery, venule or arteriole, via, e.g., hydrodynamic injection or catheterization. In some embodiments RNAi agents such as siRNA can delivered locally to specific organs or by systemic administration.

Pharmaceutical Compositions

In one embodiment, the agent described herein is an active ingredient in a composition comprising a pharmaceutically acceptable carrier (referred to herein as a pharmaceutical composition). Such a composition is referred to herein as a pharmaceutical composition. A "pharmaceutically acceptable carrier" means any pharmaceutically acceptable means to mix and/or deliver the targeted delivery composition to a subject. The term "pharmaceutically acceptable carrier" as used herein means a pharmaceutically acceptable material, composition or vehicle, such as a liquid or solid filler, diluent, excipient, solvent or encapsulating material, involved in carrying or transporting the subject agents from one organ, or portion of the body, to another organ, or portion of the body. Each carrier must be "acceptable" in the sense of being compatible with the other ingredients of the composition and is compatible with administration to a subject, for example a human. Such compositions can be specifically formulated for administration via one or more of a number of routes, such as the routes of administration described herein. Supplementary active ingredients also can be incorporated into the compositions. When an agent, formulation or pharmaceutical composition described herein, is administered to a subject, preferably, a therapeutically effective amount is administered. As used herein, the term "therapeutically effective amount" refers to an amount that results in an improvement or remediation of the condition.

Administration

Administration of the pharmaceutical composition is by means which the agent contained therein will contact the target cell or tissue (e.g., tumor or cancer). Examples of such routes are localized and systemic, which include, without limitation parenteral, enteral, and topical administration. Parenteral administration is usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, intratumoral, and intrasternal injection and infusion. Administration can be systemic administration, or localized, as determined necessary by the skilled practitioner. Localized administration can be directed to the location of the target tissue. Pharmaceutical compositions and formulations for specified modes of administration, described herein are also encompassed by the present invention. The compounds of the invention can be administered parenterally by injection or by gradual infusion over time and can be delivered by peristaltic means.

The agents described herein are administered to a subject by routes and in formulations that will deliver the agent to tumor tissue or cells of the subject. Delivery to the tumor cell refers to eventual contacting of the cancer cells by the agent, in a manner required for the agent to exert the intended effect. For instance, an antibody or antigen binding fragment thereof is administered by a route, and in a formulation, that promotes contact with the Fzd2 receptor located on the exterior (extracellular location) of the cancer cells. The amount delivered to the subject is sufficient to promote an effective amount of the agent being delivered to the cancer cells. The route of administration will depend upon various factors, including the location of the cancer cells, the desired final concentration at the cancer cell. Preferred routes and levels of administration, as well as appropriate formulations, will be determined by the skilled practitioner for each individual subject.

Administration may be by transmucosal or transdermal means. For transmucosal or transdermal administration, penetrants appropriate to the barrier to be permeated are used in the formulation. Such penetrants are generally known in the art, and include, for example, for transmucosal administration bile salts and fusidic acid derivatives. In addition, detergents may be used to facilitate permeation. Transmucosal administration may be through nasal sprays, for example, or using suppositories. For oral administration, the compounds of the invention are formulated into conventional oral administration forms such as capsules, tablets and tonics.

For topical administration, the pharmaceutical composition is formulated into ointments, salves, gels, or creams, as is generally known in the art.

The therapeutic compositions of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered and timing depends on the subject to be treated, capacity of the subject's system to utilize the active ingredient, and degree of therapeutic effect desired. Precise amounts of active ingredient required to be administered depend on the judgment of the practitioner and are peculiar to each individual.

Typically the agent is administered to a subject as a pharmaceutical composition. A pharmaceutical composition contains the active agent, described herein, and a pharmaceutically acceptable carrier. The composition may further comprise one or more additional ingredients, such as additional active agents.

The pharmaceutical composition formulation can further comprise ingredients for protection of the active agent in the administered physiological and cellular environment. For example, the formulation may contain an ingredient to protect the agent from degradation by digestive enzymes, or from attack by the immune system of the subject.

As used here, the term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used here, the term "pharmaceutically-acceptable carrier" means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, methylcellulose, ethyl cellulose, microcrystalline cellulose and cellulose acetate; (4) powdered tragacanth; (5) malt; (6) gelatin; (7) lubricating agents, such as magnesium stearate, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol (PEG); (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; (22) C2-C12 alcohols, such as ethanol; and (23) other non-toxic compatible substances employed in pharmaceutical formulations. Wetting agents, coloring agents, release agents, coating agents, sweetening agents, flavoring agents, perfuming agents, preservative and antioxidants can also be present in the formulation. The terms such as "excipient", "carrier", "pharmaceutically acceptable carrier" or the like are used interchangeably herein.

Downmodulatory agents of Fzd2 (e.g., Anti-Fzd2 peptides and/or Abs) of the present invention can be administered either as individual therapeutic agents or in combination with other therapeutic agents. They can be administered alone, but are generally administered with a pharmaceutical carrier selected on the basis of the chosen route of administration and standard pharmaceutical practice.

The dosage administered will, of course, vary depending upon known factors such as the pharmacodynamic characteristics of the particular agent, and its mode and route of administration; age, health, and weight of the recipient; nature and extent of symptoms, kind of concurrent treatment, frequency of treatment, and the effect desired. Usually a daily dosage of active ingredient can be about 0.01 to 100 milligrams per kilogram of body weight. Ordinarily 1.0 to 5, and preferably 1 to 10 milligrams per kilogram per day given in divided doses 1 to 6 times a day or in sustained release form is effective to obtain desired results.

Dosage forms (composition) suitable for internal administration generally contain from about 0.1 milligram to about 500 milligrams of active ingredient per unit. In these pharmaceutical compositions the active ingredient will ordinarily be present in an amount of about 0.5 to 95% by weight based on the total weight of the composition.

As a non-limiting example, treatment of cancer by the methods described herein in humans or animals can be provided as a daily dosage of a pharmaceutical composition comprising anti-Fzd2 peptides, monoclonal chimeric and/or murine antibodies of the present invention at a dosage of 0.1 to 100 mg/kg, such as 0.5, 0.9, 1.0, 1.1, 1.5, 2, 3, 4, 5, 6, 7, 8, 9, 10, 11, 12, 13, 14, 15, 16, 17, 18, 19, 20, 21, 22, 23, 24, 25, 26, 27, 28, 29, 30, 40, 45, 50, 60, 70, 80, 90 or 100 mg/kg, per day, on at least one of day 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40, or alternatively, at least one of week 1, 2, 3, 4, 5, 6, 7, 8, 9, 10, 11, 12, 13, 14, 15, 16, 17, 18, 19 or 20, or any combination thereof, using single or divided doses of every 24, 12, 8, 6, 4, or 2 hours, or any combination thereof.

For parenteral administration, anti-Fzd2 antibodies or antigen binding fragments can be formulated as a solution, suspension, emulsion or lyophilized powder in association with a pharmaceutically acceptable parenteral vehicle. Examples of such vehicles are water, saline, Ringer's solution, dextrose solution, and 5% human serum albumin. Liposomes and non-aqueous vehicles such as fixed oils can also be used. The vehicle or lyophilized powder can contain additives that maintain isotonicity (e.g., sodium chloride, mannitol) and chemical stability (e.g., buffers and preservatives). The formulation is sterilized by commonly used techniques.

DEFINITIONS

Downmodulation refers to reducing one or more functions of the protein (Fzd2) (e.g., ligand binding, signal transduction, etc.). This can be accomplished by directly inhibiting the production of functional Fzd2 itself in the cell (e.g., by reducing gene expression or protein synthesis), and/or by reducing Fzd2 function/activity. Fzd2 function/activity can be reduced, for example by directly inhibiting the Fzd2 protein itself (e.g. by inhibiting ligand binding) or otherwise targeting that protein for degradation. As such, an agent useful in the present invention is one that inhibits Fzd2 gene expression or protein synthesis, or inhibits one or more Fzd2 function or activity.

Downmodulation may be accomplished by a reduction of the amount of a receptor on the surface of a cell (e.g., by promotion of internalization of the receptor). In one aspect of the invention the level of Fzd2 expressed on the surface of a cell is reduced by contacting the cell with an agent that downmodulates Fzd2 in the cell. In one embodiment, the agent binds specifically to Fzd2 of the cell and promotes internalization of the Fzd2 by the cell. Such agents are described herein. A significant amount of downmodulation is expected to produce useful results in the methods described herein. In one embodiment, downmodulation results in at least 5%, at least 10%, at least 20%, at least 30%, at least 40%, or at least 50%, or at least 60%, or at least 70%, or at least 80%, or at least 90%, or at least 99% reduction in the level of Fzd2 protein or mRNA in the cell by the methods described herein, as compared to that typically observed or expected in the absence of treatment.

As used herein, the term "treating" and "treatment" and/or "palliating" refers to administering to a subject an effective amount of the agent, so as to inhibit Fzd2 (e.g., promote receptor internalization and/or inhibit ligand binding), such that the subject has an improvement in the condition, for example, detectable beneficial or desired clinical results. For purposes of this invention, beneficial or desired clinical results include, but are not limited to, a decrease in the severity of the symptoms, including partial or complete alleviation of one or more symptoms; prevention or delay in the development of one or more indicators, symptoms, or markers; diminishment of extent of discomfort (i.e., not worsening) incurred by the condition; slowing of progression of the condition, amelioration or palliation of the condition, and also complete recovery from the condition. A decrease in onset of one or more indicators, symptoms, markers of the tumor or cancer as described herein may be by at least 5%, at least 10%, at least 20%, at least 30%, at least 40%, or at least 50%, or at least 60%, or at least 70%, or at least 80%, or at least 90%, or at least 99% that typically observed or expected in the absence of treatment. In one embodiment, the onset of one or more symptoms, indicators or markers is completely prevented. In one embodiment, one or more of the symptoms of the tumor or cancer experienced prior to administration are alleviated by at least 5%, at least 10%, at least 20%, at least 30%, at least 40%, or at least 50%, or at least 60%, or at least 70%, or at least 80%, or at least 90%, or at least 99% that experienced in the absence of treatment.

The term "therapeutically effective amount" refers to an amount that is sufficient to effect a therapeutically significant reduction in a symptom associated with a disease, disorder or injury being treated, when administered to a typical subject with that condition. A therapeutically significant reduction in a symptom is, e.g. about 10%, about 20%, about 30%, about 40%, about 50%, about 60%, about 70%, about 80%, about 90%, about 100%, about 125%, about 150% or more as compared to a control or non-treated subject.

The compositions as disclosed herein can be administered in prophylactically or therapeutically effective amounts. A prophylactically effective amount means that amount necessary, at least partly, to delay the onset of, inhibit the progression of, or halt altogether, the onset or progression of the particular disease or disorder being treated.

Such amounts for therapy or prophylaxis will depend, of course, on the particular condition being treated, the severity of the condition and individual patient parameters including age, physical condition, size, weight and concurrent treatment. These factors are well known to those of ordinary skill in the art and can be addressed with no more than routine experimentation. It is preferred generally that a maximum dose be used, that is, the highest safe dose according to sound medical judgment. It will be understood by those of ordinary skill in the art, however, that a lower dose or tolerable dose can be administered for medical reasons, psychological reasons or for virtually any other reasons.

As used herein, an antigen binding fragment of an antibody includes, without limitation, the Fab, scFv, Fv, dAb, and Fd fragments. Example antigen binding fragments are (i) the Fab fragment consisting of the VL, VH, CL and CH1 domains; (ii) the Fd fragment consisting of the VH and CH1 domains; (iii) the Fv fragment consisting of the VL and VH domains of a single arm of an antibody, (iv) the dAb fragment (Ward, E. S. et al., Nature 341, 544-546 (1989) which consists of a VH domain; (v) isolated CDR regions; and (vi) F(ab')2 fragments, a bivalent fragment comprising two Fab fragments linked by a disulphide bridge at the hinge region. Although the two domains of the Fv fragment are coded for by separate genes, it has proved possible to make a synthetic linker that enables them to be made as a single protein chain (known as single chain Fv (scFv); Bird, R. E. et al., Science 242, 423-426 (1988) Huston, J. S. et al., Proc. Natl. Acad. Sci., USA 85, 5879-5883 (1988)) by recombinant methods.

The term "subject" includes organisms which are capable of suffering from a disease, disorder or injury, who could otherwise benefit from the administration of a compound or composition of the invention, such as human and non-human animals. The terms subject, individual, and patient are used interchangeably herein. The term "non-human animals" of the invention includes all vertebrates, including, without limitation, mammals (e.g., rodent (mice, rat, rabbit, guinea pig), primate, canine, equine, bovine, feline, porcine) and non-mammals. Non-human primates are also possible subjects. Specific subjects include, without limitation, humans, sheep, dog, cow, horses, chickens, mice, rats, hamster, rabbit, amphibians, reptiles, etc. Cells described herein can be in the context of or otherwise isolated from any such subject described herein.

The terms "decrease", "reduced", "reduction", "decrease" or "inhibit" are all used herein generally to mean a decrease by a statistically significant amount when compared to an appropriate reference level. In one embodiment, the reduction is at least 10% as compared to a reference level, or at least about 20%, or at least about 30%, or at least about 40%, or at least about 50%, or at least about 60%, or at least about 70%, or at least about 80%, or at least about 90% or up to and including a reduction of 100% (e.g. absent level or non-detectable level as compared to a reference level).

The term "tumor cell" is used to refer to precancerous and also cancerous cells.

As used herein, the term "administer" refers to the placement of a pharmaceutically acceptable composition into a subject by a method or route which results in at least partial localization of an effective amount of the composition to a desired site (e.g., to the tumor tissue or cells of the tumor) such that desired effect is produced. A compound or composition described herein can be administered by any appropriate route known in the art including, but not limited to, oral or parenteral routes, including intravenous, intramuscular, subcutaneous, transdermal, airway (aerosol), pulmonary, nasal, rectal, and topical (including buccal and sublingual) administration.

Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebrospinal, and intrasternal injection and infusion. In preferred embodiments, the compositions are administered by intravenous infusion or injection.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%.

In one respect, the present invention relates to the herein described compositions, methods, and respective component(s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The present invention may be as defined in any one of the following numbered paragraphs.

1. A method of treating cancer in a subject comprising administering to the subject a therapeutically effective amount of an antibody or antigen binding fragment thereof that downmodulates Fzd2, such that the antibody or antigen binding fragment thereof is delivered to cancer cells of the subject, to thereby treat the cancer.

2. A method of inhibiting growth, migration and/or invasion of a cancer cell in a subject comprising administering to the subject a therapeutically effective amount of an antibody or antigen binding fragment thereof that downmodulates Fzd2, such that the antibody or antigen binding fragment thereof is delivered to the cancer cells, to thereby treat the cancer.

3. The method of any one of paragraphs 1 or 2, wherein the antibody specifically binds Fzd2.

4. The method of paragraph 3, wherein the antibody binds to Fzd2 and promotes internalization of the Fzd2 receptor by the cancer cells.
5. The method of any one of paragraph 3-4, wherein the antibody to Fzd2 prevents ligand binding to Fzd2.
6. The method of any one of paragraph 3-5, wherein the antibody specifically binds an extracellular portion of the Fzd-2 protein.
7. The method of any one of paragraphs 3-6, wherein the antibody specifically binds to Fzd2 within a region of Fzd2 corresponding to amino acids 24-247 of Fzd2.
8. The method of any one of paragraphs 3-7, wherein the antibody specifically binds to Fzd2 within a region of Fzd2 corresponding to amino acids 125-163 of Fzd2.
9. The method of any one of paragraphs 3-7, wherein the antibody specifically binds to Fzd2 within a region of Fzd2 corresponding to amino acids 134-163 of Fzd2.
10. The method of any one of paragraphs 3-7, wherein the antibody specifically binds to Fzd2 within a region of Fzd2 corresponding to amino acids 144-163 of Fzd2.
11. The method of any one of paragraphs 3-10, wherein the antibody specifically binds to the epitope HGAEQICVGQNHSEDGAPAL (SEQ ID NO: 1).
12. The method of any one of paragraphs 3-11, wherein the antibody is monoclonal.
13. The method of any one of paragraphs 3-11, wherein the antibody is polyclonal.
14. The method of any one of paragraphs 3-12, wherein the antibody is humanized.
15. The method of any one of paragraphs 1-14, wherein the cancer is selected from the group consisting of gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer.
16. The method of any one of paragraphs 1-15, wherein the cancer is liver cancer.
17. The method of any one of paragraphs 1-16, wherein the cancer is late stage hepatocellular carcinoma.
18. The method of any one of paragraphs 1-17, wherein the cancer displays overexpression of Fzd2.
19. The method of any one of paragraphs 1-18, wherein the cancer displays overexpression of Wnt5a.

The invention is further illustrated by the following examples, which should not be construed as further limiting.

EXAMPLES

Example 1

Figure 1B:
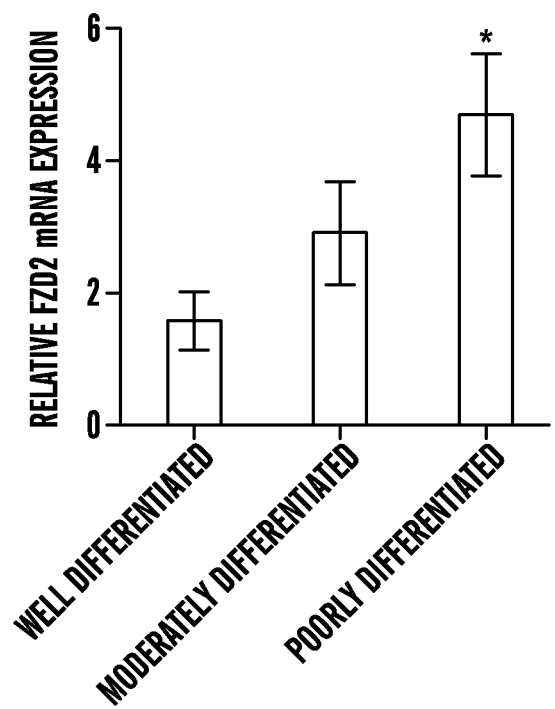
Figure 2:
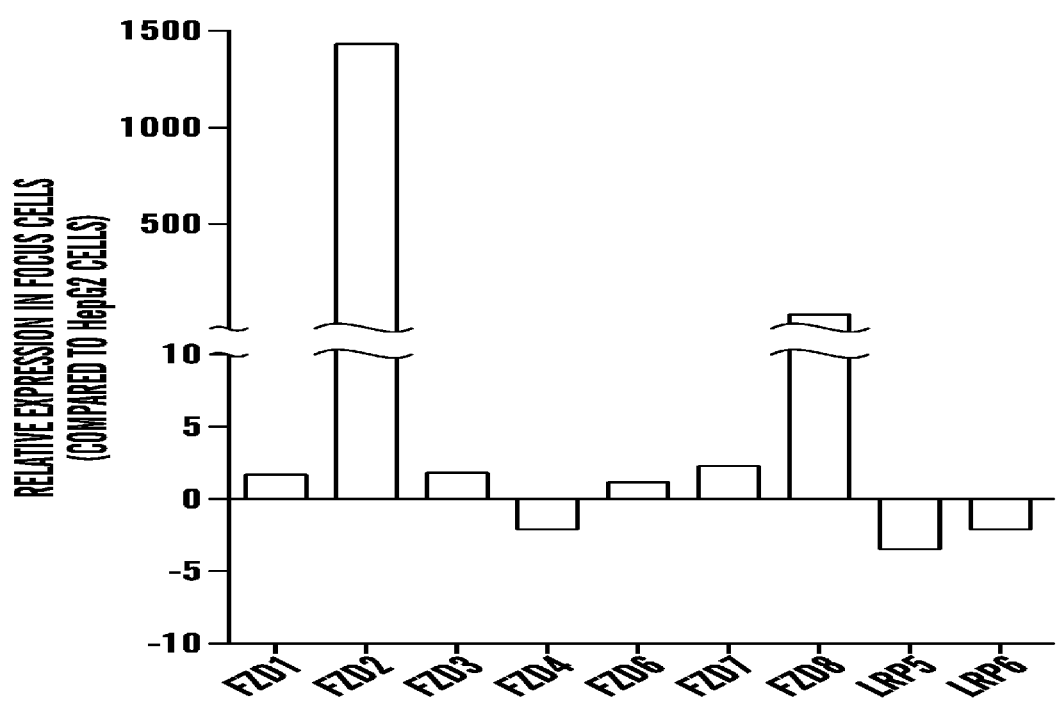
FIG. 2 shows experimental results which indicate Fzd2 is highly overexpressed in FOCUS cell line compared with more epitheliallike HepG2 HCC cell line. A bar graph showing relative mRNA expression of various Wnt signaling receptors and co-receptors in FOCUS cells compared with HepG2 cells.

Frizzled 2 Receptor as a Target for Therapeutic Antibodies in the Treatment of Hepatocellular Carcinoma Fzd2 is Overexpressed in Late Stage and Poorly Differentiated HCC Initial studies of Wnt receptor expression in hepatocellular carcinomas revealed marked overexpression of Frizzled 2 (Fzd2) in late-stage and poorly differentiated HCC (FIG. 1). The transcript levels of the Fzd2 gene were measured in 48 tissue samples obtained from patients with histopathologically confirmed HCC (stage I, n=7; stage II, n=8; stage III, n=8; stage IV, n=3; tumor lesion, n=14), as well as in normal liver samples (n=8). Fzd2 was found to be significantly overexpressed in late-stage HCC (Stage III and IV) compared with normal tissue (P<0.05). Further, the levels of Fzd2 expression correlated negatively with the degree of tissue differentiation. Moderately and poorly differentiated tumors showed higher levels of Fzd2 compared with well-differentiated tumor types. Further, we found that Fzd2 is highly overexpressed in mesenchymal-like, metastatic HCC cell line (FOCUS) compared with the more epithelial-like HepG2 HCC cell line (FIG. 2).

Fzd2 Knockdown or Treatment with an Anti-Fzd2 Antibody Reduces Cellular Migration and Invasion In Vitro.

Figure 3A:
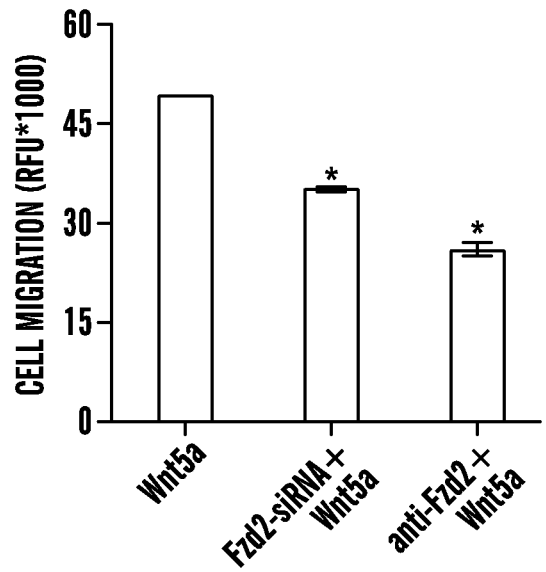
FIG. 3A-FIG. 3B show experimental results which indicate Fzd2 plays an essential role in Wnt5a-mediated cellular migration and invasion.
Figure 3B:
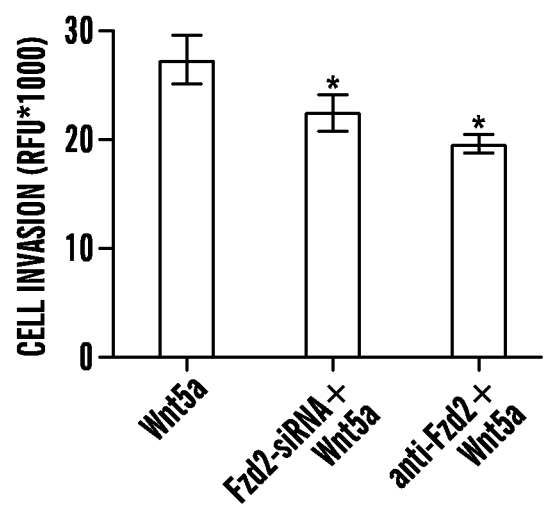

The Wnt proteins are growth factors that have been shown to play critical roles in proliferation, migration and invasion. The Wnt proteins mediate their effects through binding to and activating receptors of the Fzd family. siRNA-mediated knockdown of Fzd2 or treatment with anti-Fzd2 antibody was found to inhibit Wnt-mediated cellular migration and invasion of FOCUS cells in vitro, suggesting that Fzd2-mediated non-canonical Wnt signaling is critical for these processes (FIG. 3).

The Anti-Fzd2 Antibody Causes Internalization of Cell Surface Fzd2 Receptors

Figure 4A:
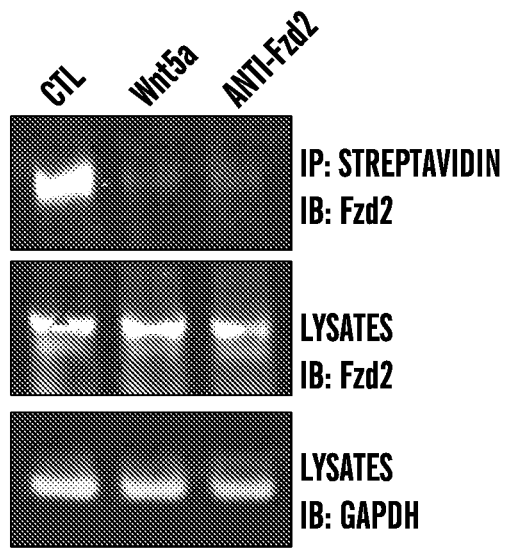
FIG. 4A-FIG. 4B show experimental results which indicate. Anti-Fzd2 antibody causes internalization of cell surface Fzd2 receptors.
Figure 4B:
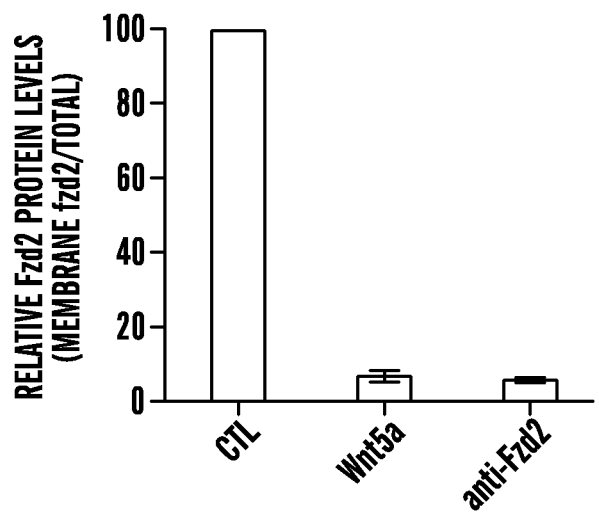

Using a cell surface biotinylation assay, it was shown that treatment of FOCUS cells with the anti-Fzd2 antibody causes internalization and degradation of Fzd2. Specifically, Fzd2 was found to be expressed at the cell membrane in the absence of its cognate ligand, Wnt5a. The protein levels of Fzd2 at the cell surface markedly decreased upon Wnt5a stimulation or treatment with the anti-Fzd2 antibody (FIG. 4).

Fzd2 Knockdown Reduces Tumor Growth in Nude Mice

Figure 5:
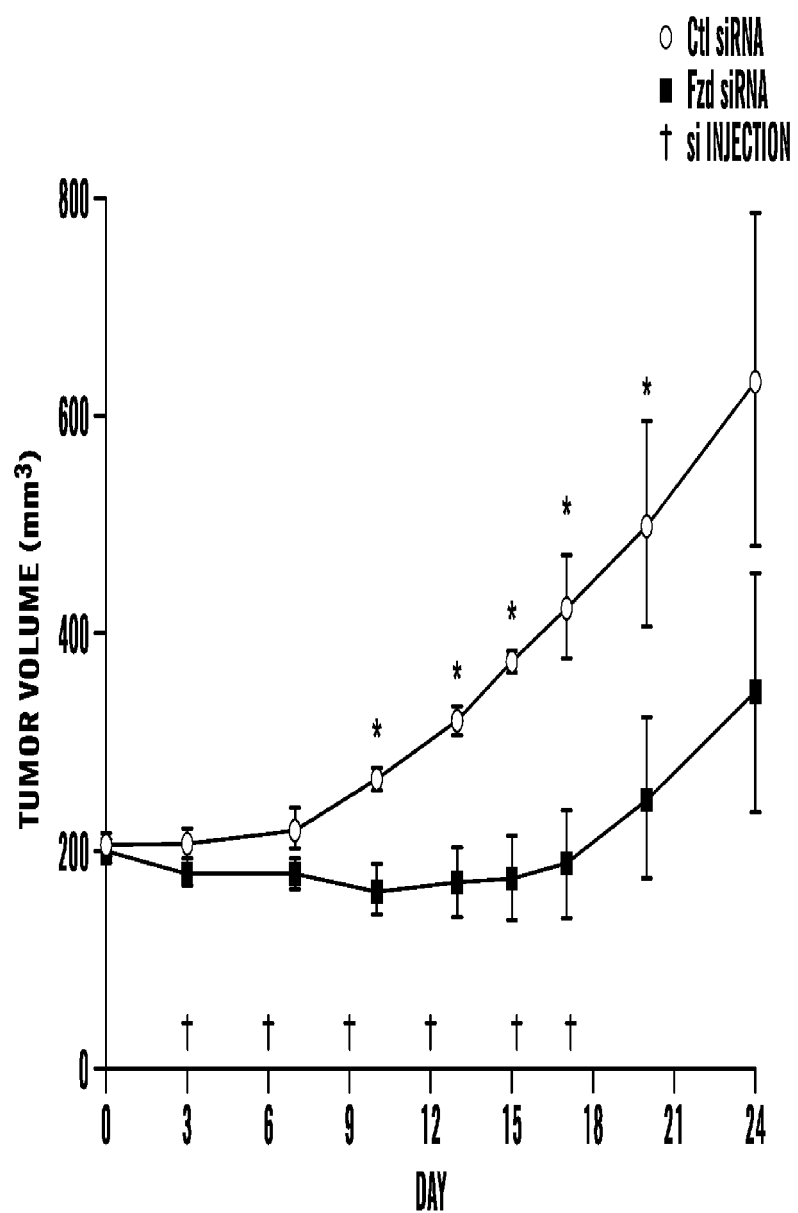
FIG. 5 shows experimental results which indicate Fzd2 knockdown reduces tumor growth in nude mice. FOCUS cells were injected s.c. into athymic mice and the ability of cells to form tumor outgrowths was monitored in the presence or absence of siRNA against Fzd2. A tumor growth curve for treated and control group showing in the presence of siRNA directed against Fzd2, tumor growth was significantly slower with a notable lag exponential growth phase is shown. Animals were injected with Fzd2-siRNA or Control.

To understand the extent of Fzd2 alterations in the pathogenesis of HCC, FOCUS were cells subcutaneously injected into athymic mice and the ability of cells to form tumor outgrowths were monitored. FOCUS cells grew rapidly in this model, producing measurable tumors by day 4. When the outgrowths were approximately 200 mm$^3$, mice were divided at random into two groups (control and treated). The treated group received Fzd2-siRNA injection on alternate days (MWF) for two weeks, while the control group received s.c injection of in-vivo transfection reagent only. In the presence of siRNA directed against Fzd2, tumor growth was significantly slower with a notable lag in the exponential growth phase (FIG. 5). Interestingly, the tumors in the treated group started to grow rapidly when the Fzd2-siRNA injections were discontinued. These data suggest that the highly tumorigenic potential of FOCUS cells is, in part, mediated through Fzd2.

Overall, the in vitro and in vivo data suggest that Fzd2 is an oncogene in HCC and that overexpression of Fzd2 contributes to the progression and metastasis of HCC.

Epitope Mapping of Anti-Fzd2 Antibody

Figure 6A:
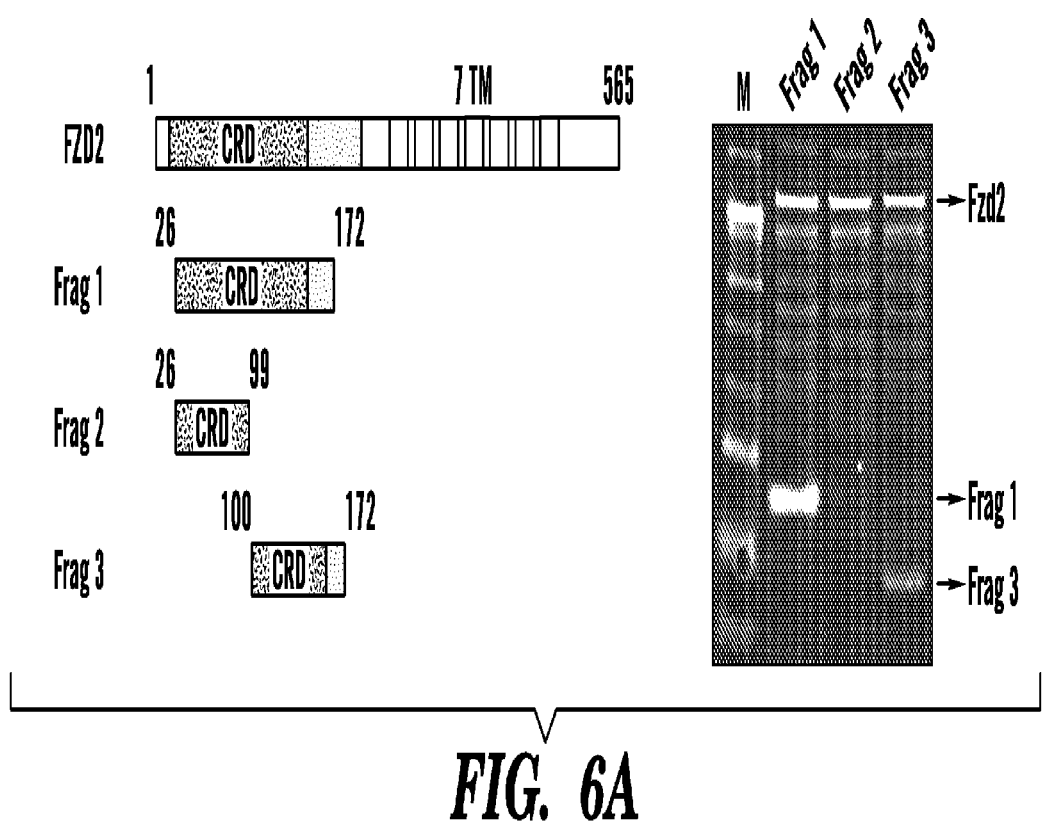
FIG. 6A-FIG. 6B show experimental results which indicate Epitope mapping of anti-Fzd2 antibody.
Figure 6B:
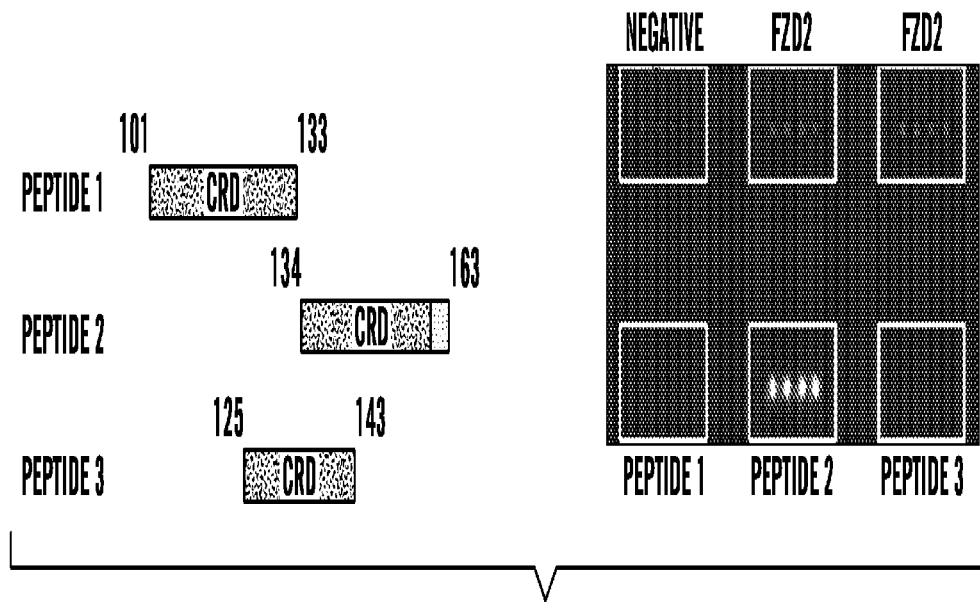

To map the epitope of anti-Fzd2 antibody (R & D Systems; MAB1307), three overlapping constructs spanning from residues 26-172 in the N-terminus region of Fzd2 were designed (FIG. 6A). When overexpressed in HEK293 cells, only the fragment 1 (full length, aa 26-172) and fragment 3 (C-terminus region, aa 100-172) were recognized by anti-Fzd2 antibody suggesting that the epitope of anti-Fzd2 antibody lies within the Fragment 3 region (FIG. 6A). To further map the epitope of anti-Fzd2 antibody, three overlapping peptides spanning Fragment 3 were synthesized. Using the peptide array, only Peptide 2 (aa 134-163) was seen to be recognized by the anti-Fzd2 antibody (FIG. 6B). Since, anti-Fzd2 antibody did not recognize Peptide 1 (aa 100-132) or overlapping Peptide 2 (aa 125-143), the epitope for anti-Fzd2 antibody was determined to lie within the residues 134-ERLRCEHFPRHGAEQICVGQNHSEDGAPAL-163 (SEQ ID NO: 1) in the N-terminus region of Fzd2. This epitope lies in the region which is highly specific to Fzd2 and does not share homology with other Fzd family members suggesting high specificity of anti-Fzd2 antibody. These sequences correspond to that shown for human fzd-2 in NCBI reference NP_001457.

Materials and Methods

Cell Lines and Reagents

Liver cancer cell line HepG2 and HEK 293T cells were obtained from American Type Culture Collection (ATCC, Rockville, Md.). FOCUS cells were obtained from J. Wands (Brown University) and have been described previously [5]. All cell lines were maintained in Dulbecco's Modified Eagle Medium (DMEM) supplemented with 10% (v/v) fetal bovine serum (FBS), 2 mM glutamine, 100 IU/mL penicillin, and 100 µg/mL streptomycin.

Signal Silence Fzd2 siRNA was purchased from Santa Cruz Biotechnology (Santa Cruz, Calif.). siRNA was introduced into cells using Lipofectamine 2000 (Invitrogen) according to the manufacturer's instructions. Recombinant human Wnt5a was from R&D Systems (Minneapolis, Minn.). Primary antibodies were obtained from the following sources: rabbit anti-β-catenin (Cell Signaling Technology), goat anti-Fzd2 (Santa Cruz Biotechnology), rat anti-Fzd2 (R&D Systems), rabbit anti-Fzd2 (Abcam).

RNA Extraction and Quantitative Real-Time PCR

HepG2 and FOCUS cells were serum-starved for 24 h and total cellular RNA was isolated using an RNeasy Mini Kit (QIAGEN, Santa Clara, Calif.). mRNA levels for the 84 Wnt-related genes were determined using the RT2 Profiler™ qPCR array (SA Biosciences Corporation, Frederick, Md.). Briefly, 1 µg of total RNA was reverse transcribed into first strand cDNA using an RT2 First Strand Kit (SA Biosciences). The resulting cDNA was subjected to qPCR using human gene-specific primers for 96 different genes, including the 84 Wnt-related genes and five housekeeping genes (B2M, HPRT1, RPL13A, GAPDH, and ACTB). The qPCR reaction was performed with an initial denaturation step of 10 min at 95° C., followed by 15 s at 95° C. and 60 s at 60° C. for 40 cycles using an Mx3000P™ QPCR system (Stratagene, La Jolla, Calif.).

The mRNA levels of each gene were normalized relative to the mean levels of the five housekeeping genes and compared with the data obtained from unstimulated, serum-starved cells using the 2-ΔΔCt method. According to this method, the normalized level of a mRNA, X, is determined using equation 1: (1)

$$X = 2^{-C_t(GOI)/2 - C_t(CTL)} \quad (1)$$

where Ct is the threshold cycle (the number of the cycle at which an increase in reporter fluorescence above a baseline signal is detected), GOI refers to the gene of interest, and CTL refers to a control housekeeping gene. This method assumes that Ct is inversely proportional to the initial concentration of mRNA and that the amount of product doubles with every cycle.

TissueScan Oncology Panel Arrays

A collection of 48 cDNA samples derived from tumor biopsies was obtained from OriGene Technologies Inc. (Rockville, Md.). The samples represented all four stages of liver carcinoma, as well as normal tissue. Gene expression was assessed by qPCR as described above. The cancer data were normalized relative to the data collected from the normal tissue samples and analyzed using the Kruskal-Wallis test at a significance level of 0.05.

Cell Migration Assay

Cell migration was assessed using a QCM™ chemotaxis 96-well cell migration assay kit (Chemicon, Temecula, Calif.). Briefly, FOCUS cells transiently transfected with Fzd2-siRNA or Control siRNA for 48 hours were suspended in DMEM and plated in the top chamber. DMEM containing Wnt5a (200 ng/mL) was added to the bottom chamber for 2 hours. Migratory cells in the bottom chamber were dissociated from the membrane, lysed, and quantified by adding CyQuant GR dye. Measurements were performed in triplicate and normalized to control cells.

Similar cell migration assays were performed utilizing the anti-Fzd2 antibody in place of transient transfection with the Fzd2-siRNA to inhibit Fzd2. The anti-Fzd2 antibody was added to the cell culture medium to a final concentration of 10 µg/ml for 2 hours prior to the migration assays.

Cell Invasion Assay

Cell invasion assay was measured using a CytoSelect™ Cell Invasion Assay (Cell Biolabs) according to the manufacturer's instructions. Briefly, FOCUS cells transiently transfected with Fzd2-siRNA or Control siRNA for 48 hours were seeded and allowed to invade towards Wnt5a (200 ng/mL) for two hours. Invasive cells, on the bottom of the invasion membrane, were stained and then quantified by adding CyQuant GR dye. Measurements were performed in triplicate and normalized to control cells.

Similar cell invasion assays were performed utilizing the anti-Fzd2 antibody in place of transient transfection with the Fzd2-siRNA to inhibit Fzd2. The anti-Fzd2 antibody was added to the cell culture medium to a final concentration of 10 µg/ml for 2 hours prior to the migration assays.

Surface Biotynlation Assay

Biotinylation of surface proteins was performed as described [6]. Briefly, FOCUS cells treated with either PBS (Control) Wnt5a (100 ng/ml) or Anti-Fzd2 antibody (10 µg/ml final concentration) for 1 hour were washed twice with PBS containing 1 mM MgCl2 and 0.1 mM CaCl2 and incubated in biotinylation buffer (154 mM NaCl, 10 mM Hepes [pH 7.6], 3 mM KCl, 1 mM MgCl2, 0.1 mM CaCl2, 10 mM glucose, 0.5 mg/ml EZ Link Sulfo HNS-SS-Biotin (Thermo Scientific, Rockford, Ill.) for 40 minutes at 4° C. Cells were then incubated in PBS containing 100 mM glycine for 5 minutes at 4° C., followed by one wash in PBS containing 1 mM MgCl2 and 0.1 mM CaCl2. Cells were lysed, and total protein concentration was determined using the BCA protein assay (Pierce, Rockford, Ill.). Biotinylated proteins were immunoprecipitated with streptavidin beads and total surface Fzd2 determined by SDS-PAGE and western blotting, as described below.

Tumorigenicity in Nude Mice

All in vivo experiments were performed using 6-week-old to 8-week-old athymic nude mice (NIH. Mice were maintained in laminar flow rooms with constant temperature and humidity. FOCUS cells were inoculated s.c. into each flank of the mice. Cells ($2 \times 10^6$ in suspension) were injected on day 0, and tumor growth was followed every 2 to 3 days by tumor diameter measurements using vernier calipers. Tumor volumes (V) were calculated using the formula: V=AB2/2 (A, axial diameter; B, rotational diameter). When the outgrowths were approximately 200 mm$^3$, mice were divided at random into two groups (control and treated). The treated group received Fzd2-siRNA injection on alternate days (MWF) for two weeks, while the control group received s.c injection of in-vivo transfection reagent only. In the presence of siRNA directed against Fzd2, tumor growth was significantly slower with a notable lag in the exponential growth phase.

Protein Isolation and Quantitative Western Blotting

Cells were rinsed in Phosphate Buffered Saline (PBS) and lysed in Lysis Buffer (20 mM Tris-HCl, 150 mM NaCl, 1% Triton X-100 (v/v), 2 mM EDTA, pH 7.8 supplemented with 1 mM sodium orthovanadate, 1 mM phenylmethylsulfonyl fluoride (PMSF), 10 µg/mL aprotinin, and 10 µg/mL leupeptin). Protein concentrations were determined using the BCA protein assay (Pierce, Rockford, Ill.) and immunoblotting experiments were performed using standard procedures. For quantitative immunoblots, primary antibodies were detected with IRDye 680-labeled goat-anti-rabbit IgG or IRDye 800-labeled goat-anti-mouse IgG (LI-COR Biosciences, Lincoln, Nebr.) at 1:5000 dilution. Bands were visualized and quantified using an Odyssey Infrared Imaging System (LI-COR Biosciences).

Epitope Mapping of Anti-Fzd Antibody

To map the epitope of anti-Fzd2 antibody, three overlapping fragments spanning from residues 26-172 were constructed in pcDNA3.1 mammalian expression vector. These constructs were transiently tranfected in HEK293 cells and whole cell lysates collected after 48 hours were subjected to western blotting with anti-Fzd2 antibody as described above. To further map the region of Fragment 3 (aa 100-172), three overlapping peptides were synthesized commercially (LifeTein, NJ). These peptides and lysates from HEK293 cells expressing Fzd2 full length gene or empty vector (negative) were printed on nitrocellulose coated glass slides using Aushon 2470 arrayer. The peptide array slide was blocked with 3% (v/v) BSA and probed with anti-Fzd2 antibody. Spots were visualized and quantified using an Odyssey Infrared Imaging System (LI-COR Biosciences).

REFERENCES

1. Parkin, D., F. Bray, and S. Devesa, *Cancer burden in the year 2000. The global picture.* European Journal of Cancer, 2001. 37: p. 4-66.
2. Carr, B., *Hepatocellular carcinoma: current management and future trends.* Gastroenterology, 2004. 127(5): p. S218-S224.
3. Lee, H., M. Kim, and J. Wands, *Wnt/Frizzled signaling in hepatocellular carcinoma.* Front Biosci, 2006. 11: p. 1901-1915.
4. Reya, T. and H. Clevers, *Wnt signalling in stem cells and cancer.* Nature, 2005. 434(7035): p. 843-50.
5. He, L., et al., *Establishment and characterization of a new human hepatocellular carcinoma cell line.* In Vitro, 1984. 20(6): p. 493-504.
6. Smith, C. A., et al., *The cell fate determinant numb interacts with EHD/Rme-1 family proteins and has a role in endocytic recycling.* Mol Biol Cell, 2004. 15(8): p. 3698-708.

Example 2

Wnt Receptor: A Novel Biologics Target Against Liver Cancer

Fzd2 Knockdown or Treatment with an Anti-Fzd2 Antibody Reduces Cellular Migration and Invasion In Vitro.

Knockdown of Fzd2 by RNAi or exposure of cells to an anti-Fzd2 antibody was shown to reduce cellular motility and invasiveness of HCC cells and reverts oncogenic phenotypes to a normal epithelial-like state (FIG. 8). Using a cell surface biotinylation assay, treatment of FOCUS HCC cells with an anti-Fzd2 antibody was found to cause internalization and degradation of Fzd2 (FIG. 8). Upon Wnt5a stimulation, cell surface levels of Fzd2 decreased markedly, and this down-regulation is also observed in cells treated with an anti-Fzd2 antibody. The antibody, however, does not activate downstream signaling.

Fzd2 Knockdown Induces Cytostasis in a Xenograft Model of HCC in Mice

Figure 8A:
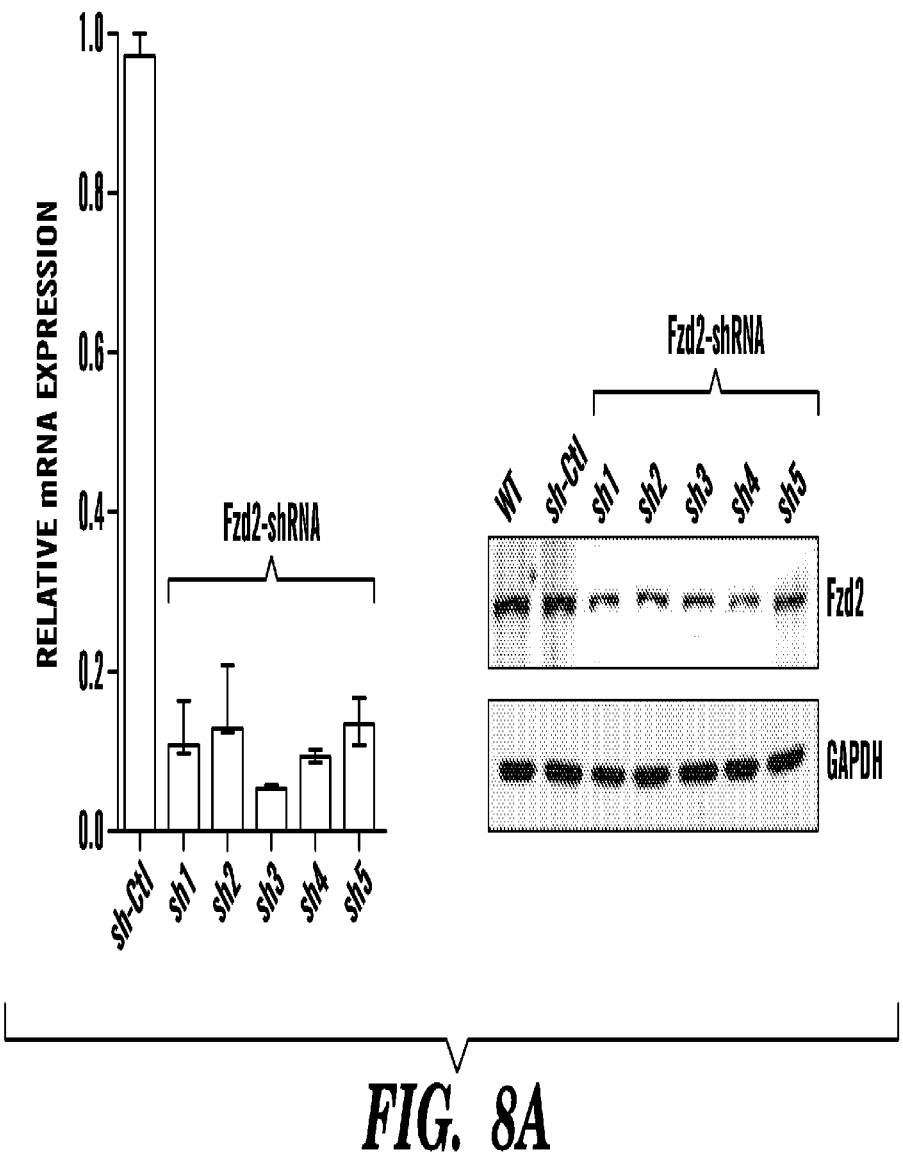
FIG. 8A-FIG. 8F show experimental results which indicate Fzd2 plays an essential role in Wnt5a-mediated cellular migration, invasion and tumor growth.
Figure 8B:
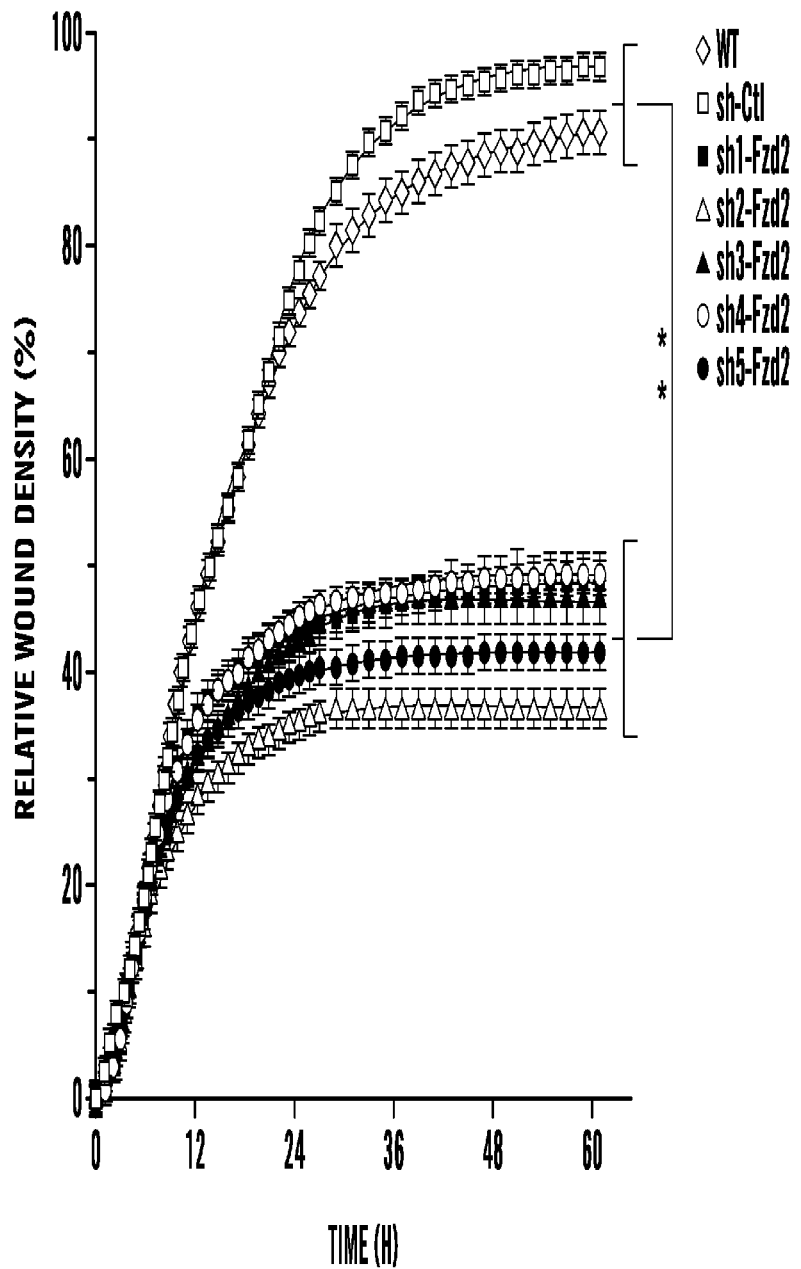
Figure 8C:
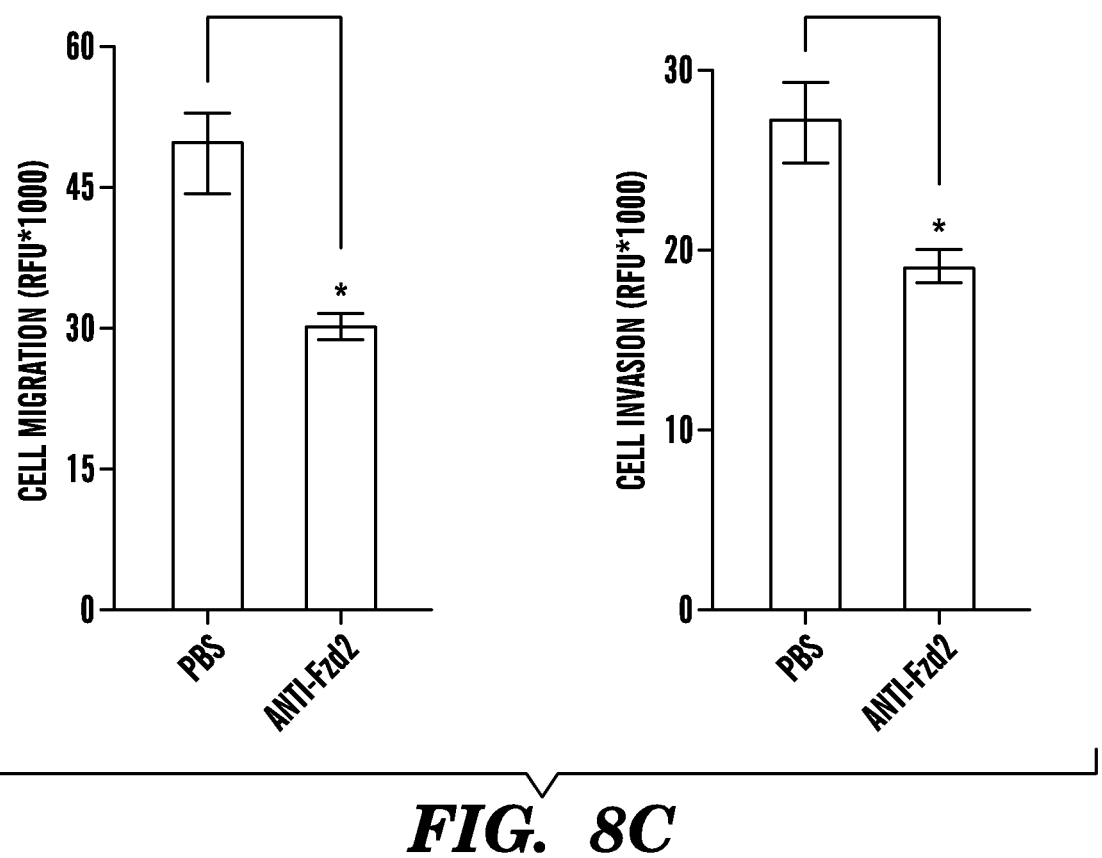
Figure 8D:
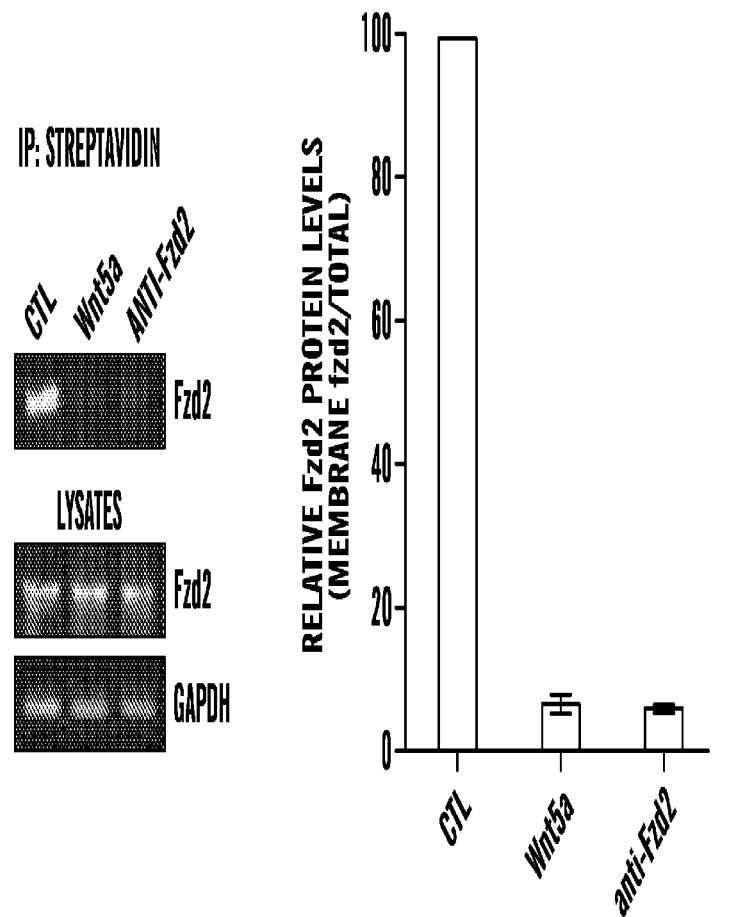
Figure 8E:
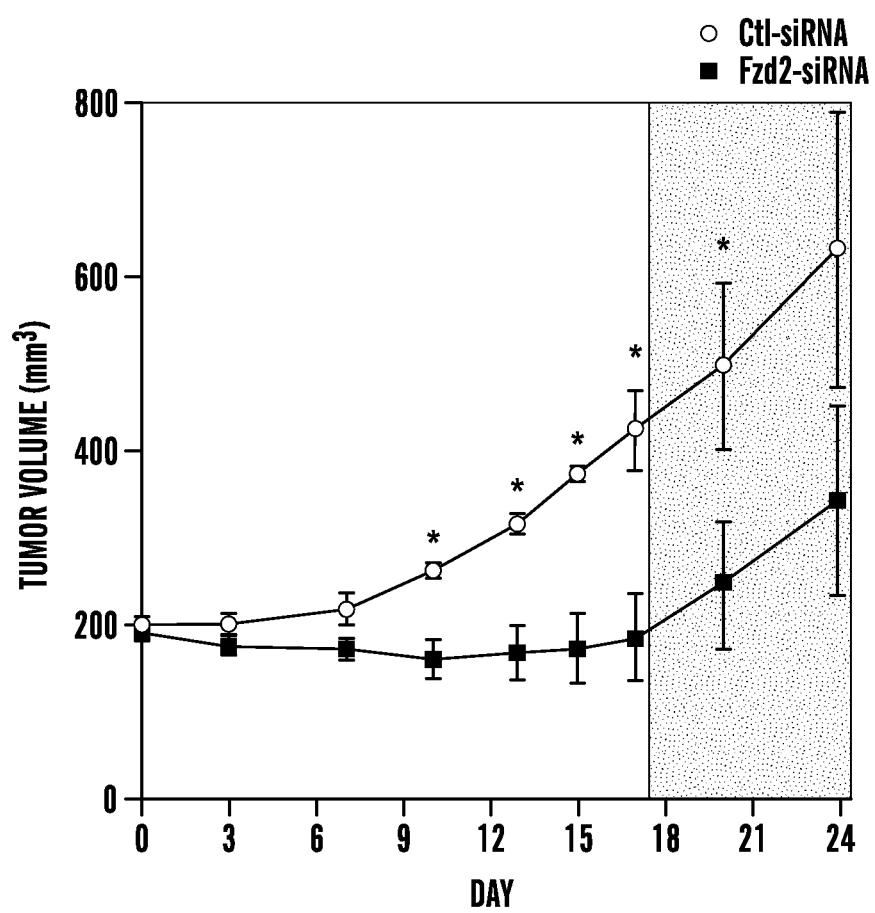
Figure 8F:
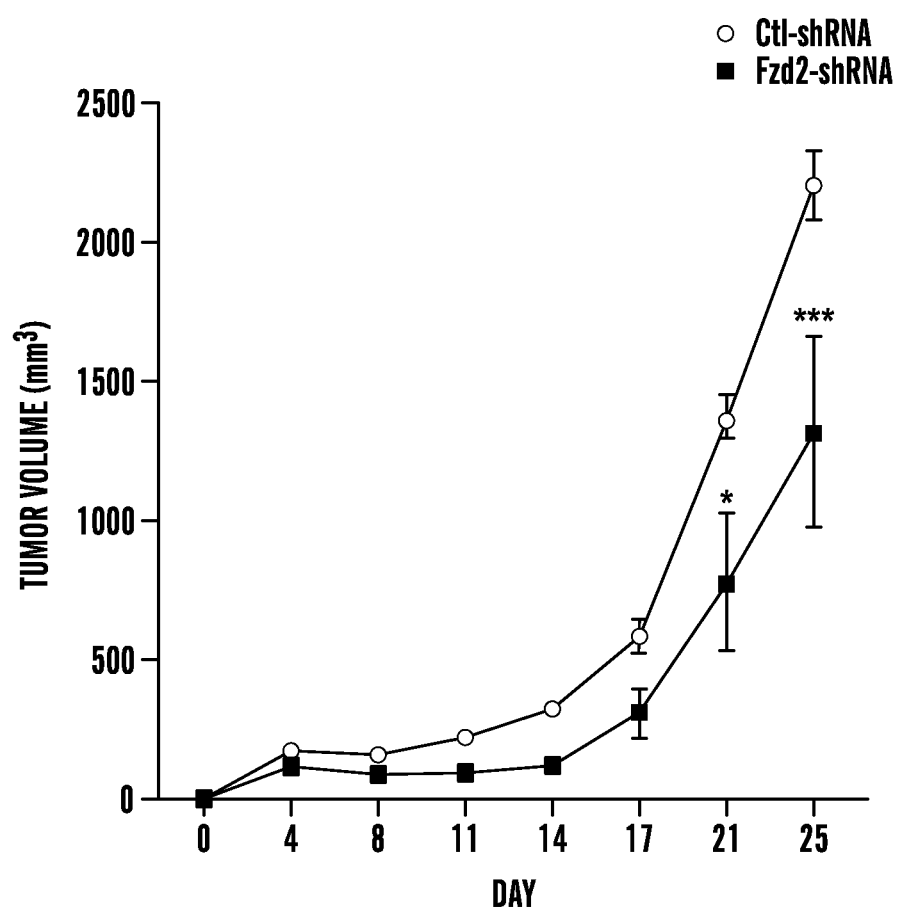

To understand the extent of Fzd2 alterations in the pathogenesis of HCC, FOCUS cells were subcutaneously injected into athymic mice and the ability of the cells to form tumor outgrowths was monitored. FOCUS cells grew rapidly in this xenograft tumor model, producing measurable tumors by day 4. When the tumors were ~200 mm$^3$, mice were divided at random into two groups (control and treated). The treated group received Fzd2-siRNA injections on alternate days (MWF) for two weeks, whereas the control group received s.c injections of in vivo transfection reagent only. In the presence of siRNA directed against Fzd2, tumor growth was significantly slower with a notable lag in the exponential growth phase (FIG. 8E). Tumors in the treated group resumed rapid growth after the Fzd2-siRNA injections were discontinued. These data suggest that the highly tumorigenic potential of FOCUS cells is, in part, mediated by Fzd2 and that Fzd2-siRNA induces cytostasis rather than cell death. Similarly, stable knockdown of Fzd2 using shRNA against Fzd2 also reduced the tumor growth in nude mice (FIG. 8F).

Overall, the in vitro and in vivo data suggest that Fzd2 is an oncogene in HCC and that overexpression of Fzd2 contributes to the progression of HCC. The fact that Fzd2 causes cytostasis rather than tumor cell death is typical of targeted drugs that bind growth factor receptors. In the case of anti-ErbB drugs, for example, it has been shown that cytostasis can result in effective tumor inhibition in human patients.

Kaplan-Meier Survival Analysis for 40 HCC Patients

Figure 9:
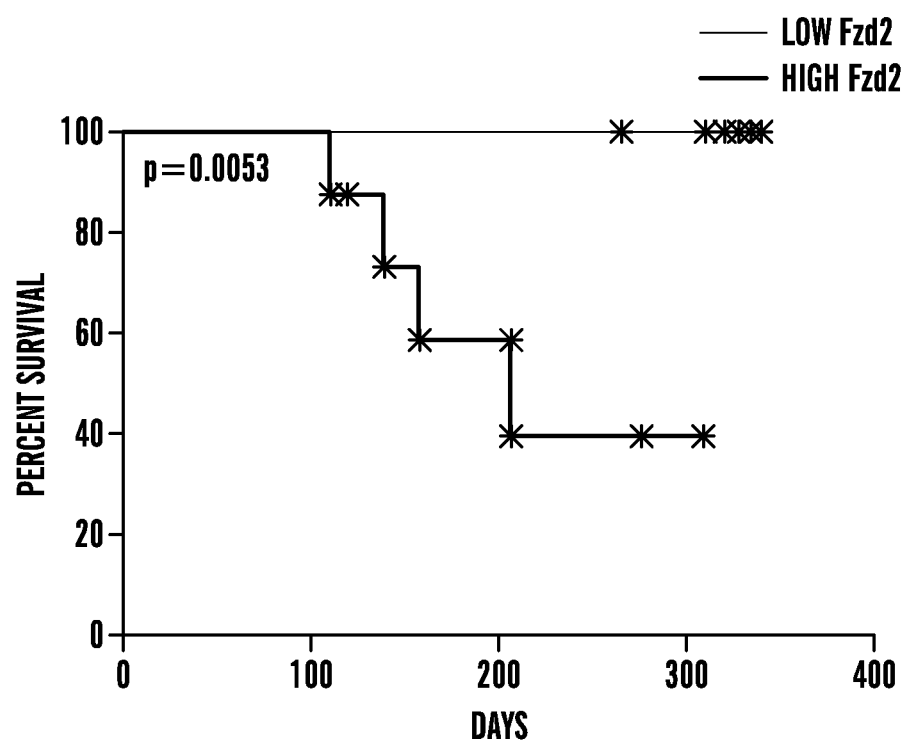
FIG. 9 shows Kaplan-Meier survival curves for 40 HCC patients. The statistical p value was generated by the Cox-Mantel log-rank test.

Kaplan-Meier survival data indicate that metastatic HCC patients had high expression of Fzd2 receptor which correlated with substantially shorter survival (p=0.0053) than metastasis-free patients who had low expression of Fzd2 (FIG. 9).

Binding Analysis of Fzd2 Specific Antibody

Figure 10:
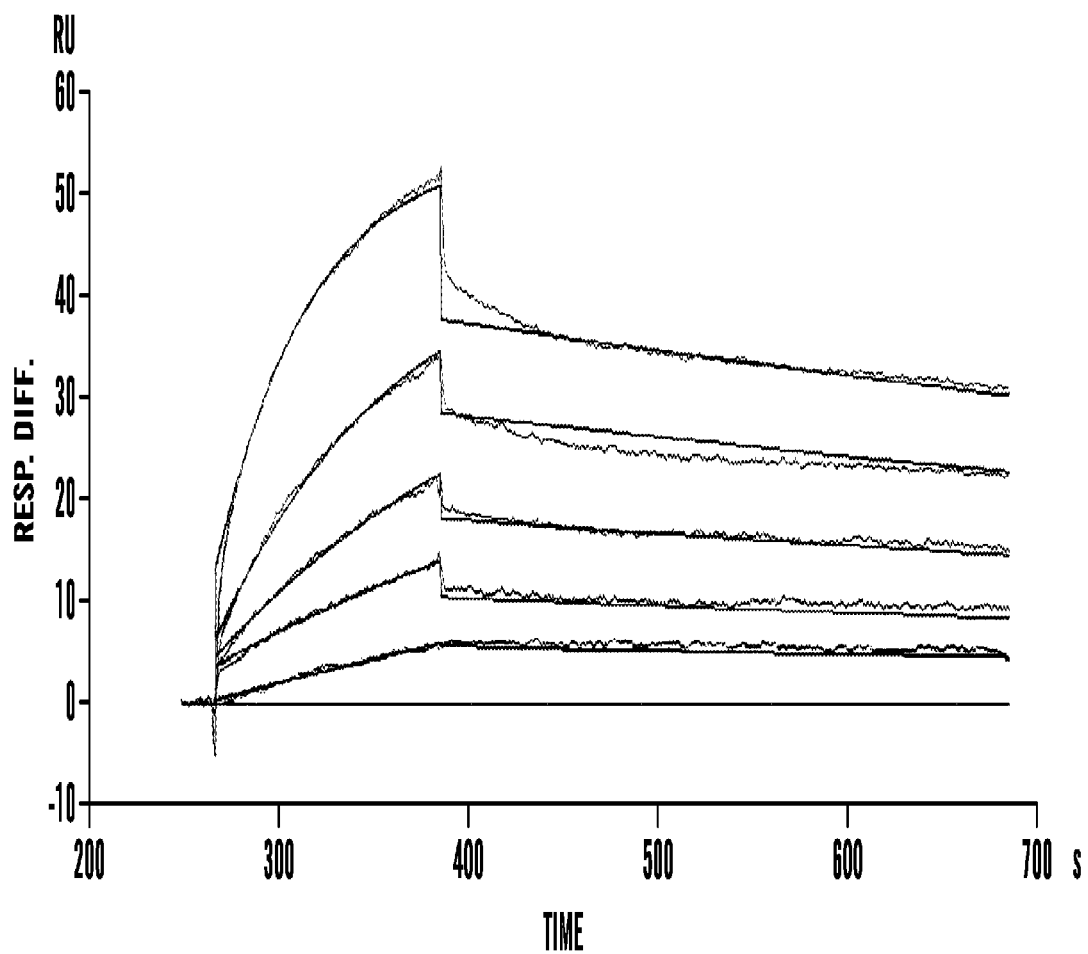
FIG. 10 is a graphical representation of binding analysis studies performed with the anti-fzd2 antibody (BioCore study performed by Precision Antibody™). The analysis indicated that the KD of the commercial Fzd2 Ab used in the experiments herein against Fzd2 is ~20 nM.

Binding analysis was performed for the epitope mapped frizzled-2 antibody (discussed in Example 1) and frizzled-2. The results of the analysis are shown below in Table 1 and FIG. 10. The antibody was determined to have high affinity binding to Fzd2 (<20 nM).

The siRNA and shRNA studies together with the Kaplan-Meier survival analysis derived from the clinical samples and outcomes of HCC patients have demonstrated that Fzd2 is an excellent target in HCC. In addition, we have shown that binding to the epitope identified here by a commercial antibody causes receptor internalization and inactivation of the downstream signaling pathway (e.g. ↓ pStat3).

TABLE 1

| Ligand | Analyte | ka (1/Ms) | kd (1/s) | Rmax (RU) | Analyte Concentration | KA (1/M) | KD (M) | Chi2 |
|---|---|---|---|---|---|---|---|---|
| Frizzled-2 Ab | Frizzled-2 | $3.9 \times 10^4$ | $7.4 \times 10^{-4}$ | 43.1 | 0-500 nM | $5.2 \times 10^7$ | $1.9 \times 10^{-8}$ | 0.45 |

Materials and Methods:

Cell Lines and Reagents

Liver cancer cell lines SNU449, SNU475, and HepG2 cells were obtained from American Type Culture Collection (ATCC, Rockville, Md.). FOCUS cells were obtained from J. Wands (Brown University) and have been described previously [1]. All cell lines were maintained in Dulbecco's Modified Eagle Medium (DMEM) supplemented with 10% (v/v) fetal bovine serum (FBS), 2 mM glutamine, 100 IU/mL penicillin, and 100 µg/mL streptomycin.

Signal Silence Fzd2 siRNA was purchased from Santa Cruz Biotechnology (Santa Cruz, Calif.). siRNA was introduced into cells using Lipofectamine 2000 (Invitrogen) according to the manufacturer's instructions. Recombinant human Wnt5a was from R&D Systems (Minneapolis, Minn.). Primary antibodies were obtained from the following sources: rabbit anti-β-catenin (Cell Signaling Technology), goat anti-Fzd2 (Santa Cruz Biotechnology), rat anti-Fzd2 (R&D Systems), rabbit anti-Fzd2 (Abcam).

Generation of Fzd2 Knockdown Stable Cell Lines

Cell lines were transfected with Fzd2-shRNA constructs (Open Biosystems) and 48 hour post-transfection selected in 4 µg/ml puramycin (Invitrogen). The clones were sorted by FACS and screened for Fzd2 knockdown by Western blot. Stable cell lines were maintained in DMEM supplemented with 10% FBS, and 2 µg/ml puramycin.

RNA Extraction and Quantitative Real-Time PCR

HepG2 and FOCUS cells were serum-starved for 24 h and total cellular RNA was isolated using an RNeasy Mini Kit (QIAGEN, Santa Clara, Calif.). mRNA levels for the 84 Wnt-related genes were determined using the RT2 Profiler™ qPCR array (SA Biosciences Corporation, Frederick, Md.). Briefly, 1 µg of total RNA was reverse transcribed into first strand cDNA using an RT2 First Strand Kit (SA Biosciences). The resulting cDNA was subjected to qPCR using human gene-specific primers for 96 different genes, including the 84 Wnt-related genes and five housekeeping genes (B2M, HPRT1, RPL13A, GAPDH, and ACTB). The qPCR reaction was performed with an initial denaturation step of 10 min at 95° C., followed by 15 s at 95° C. and 60 s at 60° C. for 40 cycles using an Mx3000P™ QPCR system (Stratagene, La Jolla, Calif.).

The mRNA levels of each gene were normalized relative to the mean levels of the five housekeeping genes and compared with the data obtained from unstimulated, serum-starved cells using the 2-ΔΔCt method. According to this method, the normalized level of a mRNA, X, is determined using equation 1: (1)

$$X = 2^{-Ct(GOI)/2 - Ct(CTL)} \quad (1)$$

where Ct is the threshold cycle (the number of the cycle at which an increase in reporter fluorescence above a baseline signal is detected), GOI refers to the gene of interest, and CTL refers to a control housekeeping gene. This method assumes that Ct is inversely proportional to the initial concentration of mRNA and that the amount of product doubles with every cycle.

Cell Migration Assay

Cell migration was assessed using a QCM™ chemotaxis 96-well cell migration assay kit (Chemicon, Temecula, Calif.). Briefly, FOCUS cells transiently transfected with Fzd2-siRNA or Control siRNA for 48 hours were suspended in DMEM and plated in the top chamber. DMEM containing Wnt5a (200 ng/mL) was added to the bottom chamber for 2 hours. Migratory cells in the bottom chamber were dissociated from the membrane, lysed, and quantified by adding CyQuant GR dye. Measurements were performed in triplicate and normalized to control cells.

Kinetic Wound-Healing Assay

The effect of Fzd2 knockdown on migration of FOCUS cells was studied using a wound-healing assay. FOCUS cells were plated on 96-well plates (Essen ImageLock, Essen Instruments, MI, US) and a wound was scratched with wound scratcher (Essen Instruments). Small molecule inhibitors at different doses were added immediately after wound scratching and wound confluence was monitored with Incucyte Live-Cell Imaging System and software (Essen Instruments). Wound closure was observed every hour for 48-72 h by comparing the mean relative wound density of at least four biological replicates in each experiment.

Cell Invasion Assay

Cell invasion assay was measured using a CytoSelect™ Cell Invasion Assay (Cell Biolabs) according to the manufacturer's instructions. Briefly, FOCUS cells transiently transfected with Fzd2-siRNA or Control siRNA for 48 hours were seeded and allowed to invade towards Wnt5a (200 ng/mL) for two hours. Invasive cells, on the bottom of the invasion membrane, were stained and then quantified by adding CyQuant GR dye. Measurements were performed in triplicate and normalized to control cells.

Surface Biotynlation Assay

Biotinylation of surface proteins was performed as described [2]. Briefly, FOCUS cells treated with either PBS (Control) Wnt5a (100 ng/ml) or Anti-Fzd2 antibody for 1 hour were washed twice with PBS containing 1 mM MgCl2 and 0.1 mM CaCl2 and incubated in biotinylation buffer (154 mM NaCl, 10 mM Hepes [pH 7.6], 3 mM KCl, 1 mM MgCl2, 0.1 mM CaCl2, 10 mM glucose, 0.5 mg/ml EZ Link Sulfo HNS-SS-Biotin (Thermo Scientific, Rockford, Ill.) for 40 minutes at 4° C. Cells were then incubated in PBS containing 100 mM glycine for 5 minutes at 4° C., followed by one wash in PBS containing 1 mM MgCl2 and 0.1 mM CaCl2. Cells were lysed, and total protein concentration was determined using the BCA protein assay (Pierce, Rockford, Ill.). Biotinylated proteins were immunoprecipitated with streptavidin beads and total surface Fzd2 determined by SDS-PAGE and western blotting, as described below.

Tumorigenicity in Nude Mice

All in vivo experiments were performed using 6-week-old to 8-week-old athymic nude mice (NIH. Mice were maintained in laminar flow rooms with constant temperature and humidity. FOCUS cells were inoculated s.c. into each flank of the mice. Cells ($2 \times 10^6$ in suspension) were injected on day 0, and tumor growth was followed every 2 to 3 days by tumor diameter measurements using vernier calipers. Tumor volumes (V) were calculated using the formula: V=AB2/2 (A, axial diameter; B, rotational diameter). When the outgrowths were approximately 200 mm$^3$, mice were divided at random into two groups (control and treated). The treated group received Fzd2-siRNA injection on alternate days (MWF) for two weeks, while the control group received s.c injection of in-vivo transfection reagent only. In the presence of siRNA directed against Fzd2, tumor growth was significantly slower with a notable lag in the exponential growth phase.

Protein Isolation and Quantitative Western Blotting

Cells were rinsed in Phosphate Buffered Saline (PBS) and lysed in Lysis Buffer (20 mM Tris-HCl, 150 mM NaCl, 1% Triton X-100 (v/v), 2 mM EDTA, pH 7.8 supplemented with 1 mM sodium orthovanadate, 1 mM phenylmethylsulfonyl fluoride (PMSF), 10 µg/mL aprotinin, and 10 µg/mL leupeptin). Protein concentrations were determined using the BCA protein assay (Pierce, Rockford, Ill.) and immunoblotting experiments were performed using standard procedures. For quantitative immunoblots, primary antibodies were detected with IRDye 680-labeled goat-anti-rabbit IgG or IRDye 800-labeled goat-anti-mouse IgG (LI-COR Biosciences, Lincoln, Nebr.) at 1:5000 dilution. Bands were visualized and quantified using an Odyssey Infrared Imaging System (LI-COR Biosciences).

Epitope Mapping of Anti-Fzd Antibody

To map the epitope of anti-Fzd2 antibody, three overlapping fragments spanning from residues 26-172 were constructed in pcDNA3.1 mammalian expression vector. These constructs were transiently tranfected in HEK293 cells and whole cell lysates collected after 48 hours were subjected to western blotting with anti-Fzd2 antibody as described above. To further map the region of Fragment 3 (aa 100-172), three overlapping peptides were synthesized commercially (LifeTein, NJ). These peptides and lysates from HEK293 cells expressing Fzd2 full length gene or empty vector (negative) were printed on nitrocellulose coated glass slides using Aushon 2470 arrayer. The peptide array slide was blocked with 3% (v/v) BSA and probed with anti-Fzd2 antibody. Spots were visualized and quantified using an Odyssey Infrared Imaging System (LI-COR Biosciences).

Kaplan-Meier Survival Analysis

Kaplan Meier survival curves of 40 HCC patients were generated using previously published dataset [3].

Cignal Finder 45-Pathway Reporter Array

Cignal™ 45-Pathway Reporter Arrays (SABiosciences, Frederick, Md.) were used to simultaneously assess 45 different signaling pathways in FOCUS cells expressing GFP or Fzd2-shRNA according to manufacturer's instructions. Briefly, reporter DNA constructs in each plate well of Cignal Finder 96-well plates were resuspended with 50 µl Opti-MEM and then mixed with 50 µl diluted Lipofectamine transfection reagent. Cells were suspended in Opti-MEM and seeded into wells (10,000 cells/well) for introducing pathway reporters into cells via reverse transfection. The cells were incubated for 48 h at 5% CO2 and 37° C. Cells were then lysed and firefly and Renilla (internal transfection control) luciferase activity were measured by quantitative luminescence assays (Dual Glo, Promega).

Generation of STAT3 Reporter Cell Line

A Cignal Lenti STAT3 Reporter kit (SABiosciences) was used to transduce lenti reporters into cells for evaluation of STAT3 pathway activation according to the manufacturer's protocols. Briefly, FOCUS cells were seeded into wells (200,000 cells/well) in 6-well plates and were grown at 37° C. for 24 h in a humidified 5% $CO_2$ incubator. Then, the cells were transduced with Lenti CMV Reporter or Lenti STAT3 Reporter (100 µl/well of lentiviral particles) and 2 ml growth medium without antibiotics containing 10 µg/ml SureEntry transduction reagent for 24 h and then incubated in fresh growth medium for another 24 h at 37° C. and 5% $CO_2$. Thereafter, the cells were treated with 4.0 µg/ml puromycin in growth medium for selection of transduced cells. The puromycin-resistant cell colonies were expanded in 100 mm cell culture dishes and maintained in DMEM supplemented with 10% FBS, and 2 µg/ml puramycin.

Cytokine Array

FOCUS cells expressing GFP-shRNA or Fzd2-shRNA were cultured in serum-free DMEM for 48 hours, and then cytokine levels in culture supernatant were detected using the Human Cytokine Array Kit (R&D Systems, Minneapolis, Minn.) per the manufacturer's protocol. Briefly, supernatants were incubated at 4 C over night with membranes arrayed with antibodies against 36 cytokines. After washing twice, membranes were incubated for 2 hours with biotin-conjugated primary anti-cytokine antibodies and then washed twice. Membranes were then incubated with IRDye 800CW Streptavidin (LI-COR) for 1 hour at room temperature, and washed twice. Signals were detected and quantified using an Odyssey Infrared Imaging System (LI-COR Biosciences).

References for Example 2

1. He, L., et al., *Establishment and characterization of a new human hepatocellular carcinoma cell line*. In Vitro, 1984. 20(6): p. 493-504.
2. Smith, C. A., et al., *The cell fate determinant numb interacts with EHD/Rme-1 family proteins and has a role in endocytic recycling*. Mol Biol Cell, 2004. 15(8): p. 3698-708.
3. Ye, Q. H., et al., *Predicting hepatitis B virus-positive metastatic hepatocellular carcinomas using gene expression profiling and supervised machine learning*. Nature medicine, 2003. 9(4): p. 416-23.

Example 3

Pharmacodynamic Biomarkers for Liver Cancer Therapeutics

It has been determined that Fzd2-mediated migration and invasion is, at least partially, due to the release of several proteases from the serine protease of the plasminogen/plasminogen activator system (PAI-1) and the family of matrix metalloproteinases (MMP2, MMP3 and MMP9). The expression and release of these proteases highly correlates with the expression of Fzd2 receptors in late-stage HCC cell lines ($p<0.01$). In addition, a novel signaling pathway downstream of Fzd2 which includes Stat3 and src family kinases, has been elucidated. Specifically, decreases in phosphorylation status of src family kinases and Stat3 as well as its transcription activity are associated with Fzd-2 knockdown by small interferences or antibody treatment. Thus, phosphorylation status of stat3 and src family kinases can be used as proximal pharmacodynamic biomarkers for Fzd2 therapeutics.

MMPs

MMPs, particularly MMPs9, 2 and 3 have been implicated in cancer for more than 40 years. In addition to their role in ECM degradation, mounting evidence suggest their role in angiogenesis, lymphangiogenesis and vasculogenesis which are critical to cancer cell invasion and metastasis. For example, MMP9 increases the bioavailability of sequestered VEGF binding to its receptor in several cancers such as colon and pancreatic cancers. MMP9 also mediates the proteolytic activation of TGF-β which is an important grow factor in HCC.

PAI-1(SerpinE1)

Plasminogen is another important system in ECM degradation. However, surprisingly high, rather than low, levels of plasminogen activator inhibitor (PAI-1) are predictive of poor survival prognosis for patients suffering from a variety of different cancers. This apparent paradoxical role of PAI-1 has demonstrated to promote tumor growth and angiogenesis both in vitro and in vivo. It has been shown that tight control of proteolytic breakdown by PAI-1 is essential for the formation of new blood vessels. In addition, by blocking the interaction between vitronectin, uPAR, and integrins, PAI-1 may induce cell detachment from the extracellular matrix and thereby promote cellular migration and tumor invasion.

sICAM-1

Expression of intracellular adhesion molecule-1 (ICAM-1) has been established to correlate with poor prognosis of solid tumors. A causal role of ICAM-1 in invasion of metastatic cancers has been shown in cancers such as breast and lung. ICAM-1 expression at the cell surface dictates a tumor's metastatic potential via recruiting and activating a series of macrophages and neutrophils which lead to the break down of endovascular and endolymphatic barriers and permit transendothelial tumor cell migration. Soluble form of ICAM-1 (sI-CAM-1) present in the circulation is a direct marker for ICAM-1 which is difficult to assess clinically.

Stat3

Deregulated expression of Stat3, a signaling molecule and a transcription factor, has been implicated in ~80% of cancer, leading to cancer cell proliferation and invasion.

Src Family Kinases

Deregulation of Src family kinases, which can phosphorylate Stat3, have been implicated in many types of cancer. The discovery of these secreted proteins and signaling molecules downstream of Fzd2 not only adds to the mechanistic details of how Fzd2 promotes tumor cell migration and invasion, but can be used as pharmacodynamic markers for therapeutics which target Fzd2 pathway Fzd2 Mediates Release of SerpinE1 and sICAM1

Figure 11A:
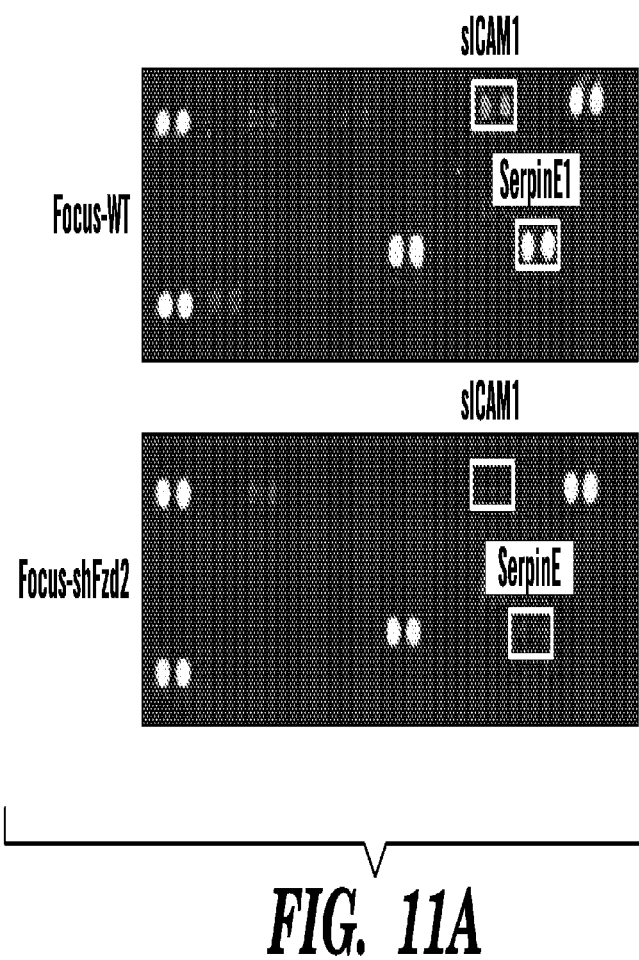
FIG. 11A-FIG. 11B show experimental results that indicate Fzd2 mediates release of SerpinE1 and sICAM1.
Figure 11B:
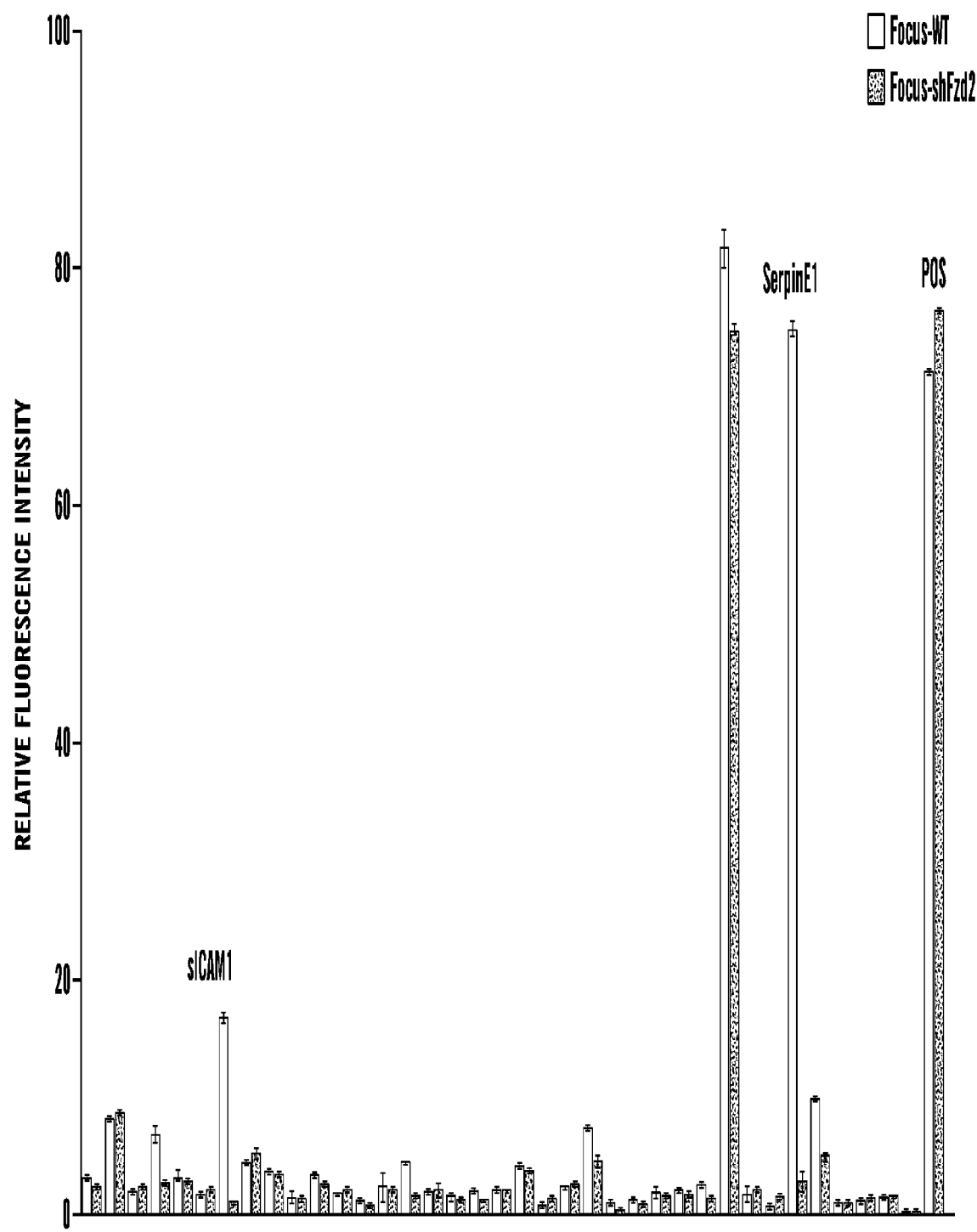

Human cytokine arrays were generated and used to analyze protein expression. The arrays consisted of antibodies spotted in duplicate onto a nitrocellulose membrane to allow high-throughput multi-analyte profiling of 36 cytokines, chemokines, and acute phase proteins in condition media. Conditioned media from FOCUS-WT or FOCUS-shFzd2 cells was mixed with a cocktail of biotinylated detection antibodies, and then incubated with the Human Cytokine Array. The array was then incubated with Infrared-800 labeled-streptavidin followed by infra-red detection using LiCor odysseys imaging system. Results of the analysis are shown in FIG. 11. Images of human cytokine array probed with conditioned media from FOCUS-WT (top of FIG. 11A) and FOCUS-shFzd2 (bottom of FIG. 11A). After detection, the array data were quantified to generate a protein profile. The abundance of 36 cytokines measured using this assay is shown in FIG. 11B. The amount of SerpinE1 and siCAM1 released was significantly lower in the condition media from FOCUS-shFzd2 cells.

Figure 12:
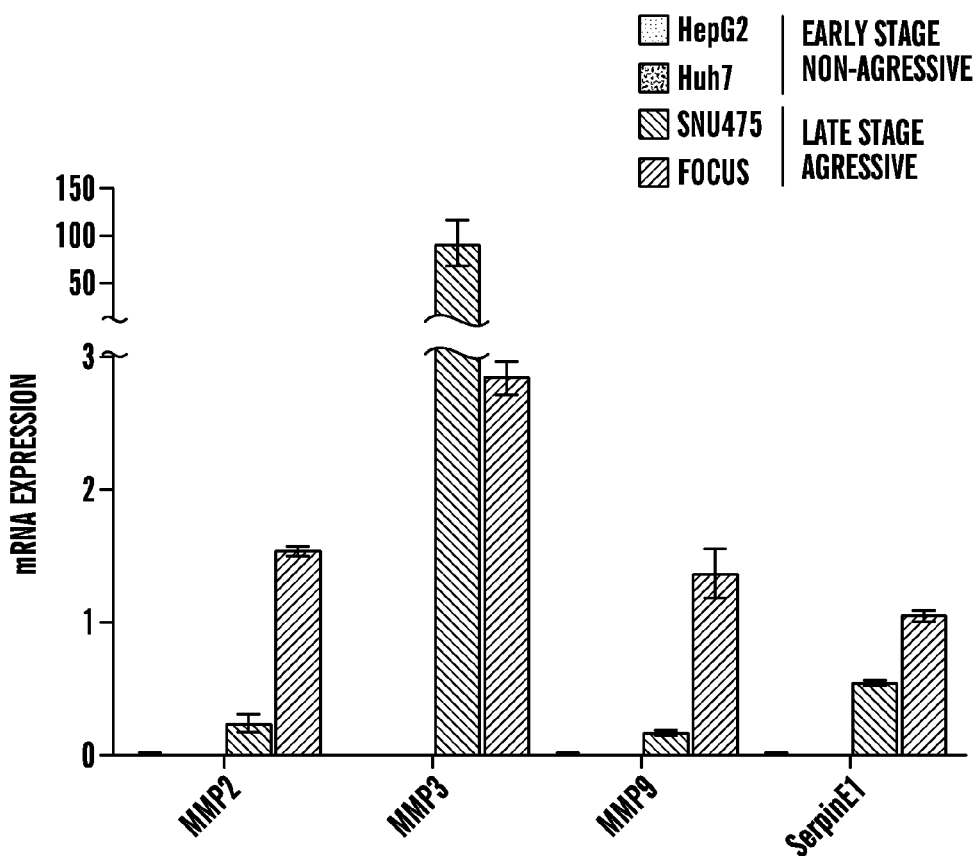
FIG. 12 shows experimental results that indicate matrix metalloproteinases (MMPs) and SerpinE1 are overexpressed in late stage, aggressive and poorly differentiated Hepatocellularcarcinoma (HCC) lines. A bar graph shows relative mRNA expression of various MMPs and SerpinE1 in early stage nonaggressive (HepG2 and Huh7) and late stage, aggressive (SNU475 and FOCUS) cell lines. mRNA expression was normalized to 18S.

Matrix Metalloproteinases (MMPs) and SerpinE1 are Overexpressed in Late Stage, Aggressive and Poorly Differentiated Hepatocellularcarcinoma (HCC) Lines Analysis was performed to examine the relative mRNA expression of various MMPs and SerpinE1 in early stage nonaggressive (HepG2 and Huh7) and late stage, aggressive (SNU475 and FOCUS) cell lines. Results are shown in FIG. 12.

Fzd2 Regulates the mRNA Expression of Matrix Metalloproteinases (MMPs) and SerpinE1

Figure 13:
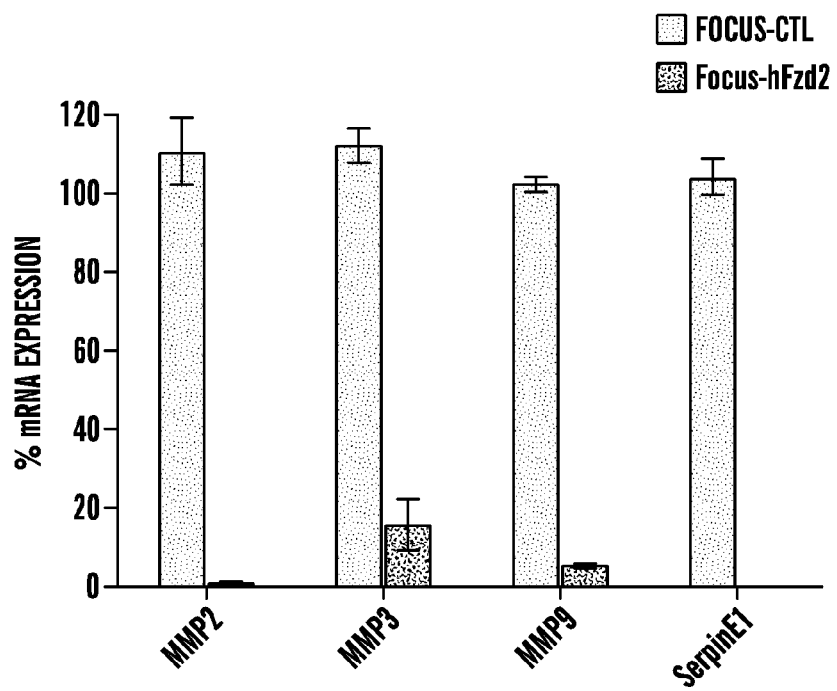
FIG. 13 shows experimental results that indicate Fzd2 regulates the mRNA expression of matrix metalloproteinases (MMPs) and SerpinE1. A bar graph shows relative mRNA expression of various MMPs and SerpinE1 in FOCUS-CTL or FOCUS-shFzd2 cells.

Analysis was performed to examine the relative mRNA expression of various MMPs and SerpinE1 in FOCUS-CTL or FOCUS-shFzd2 cells. Results are shown in FIG. 13.

Fzd2 Regulates the Phosphorylation Status of Stat3, ERK1/2 and MEK1/2 as Well as its Transcription Activity.

Figure 14A:
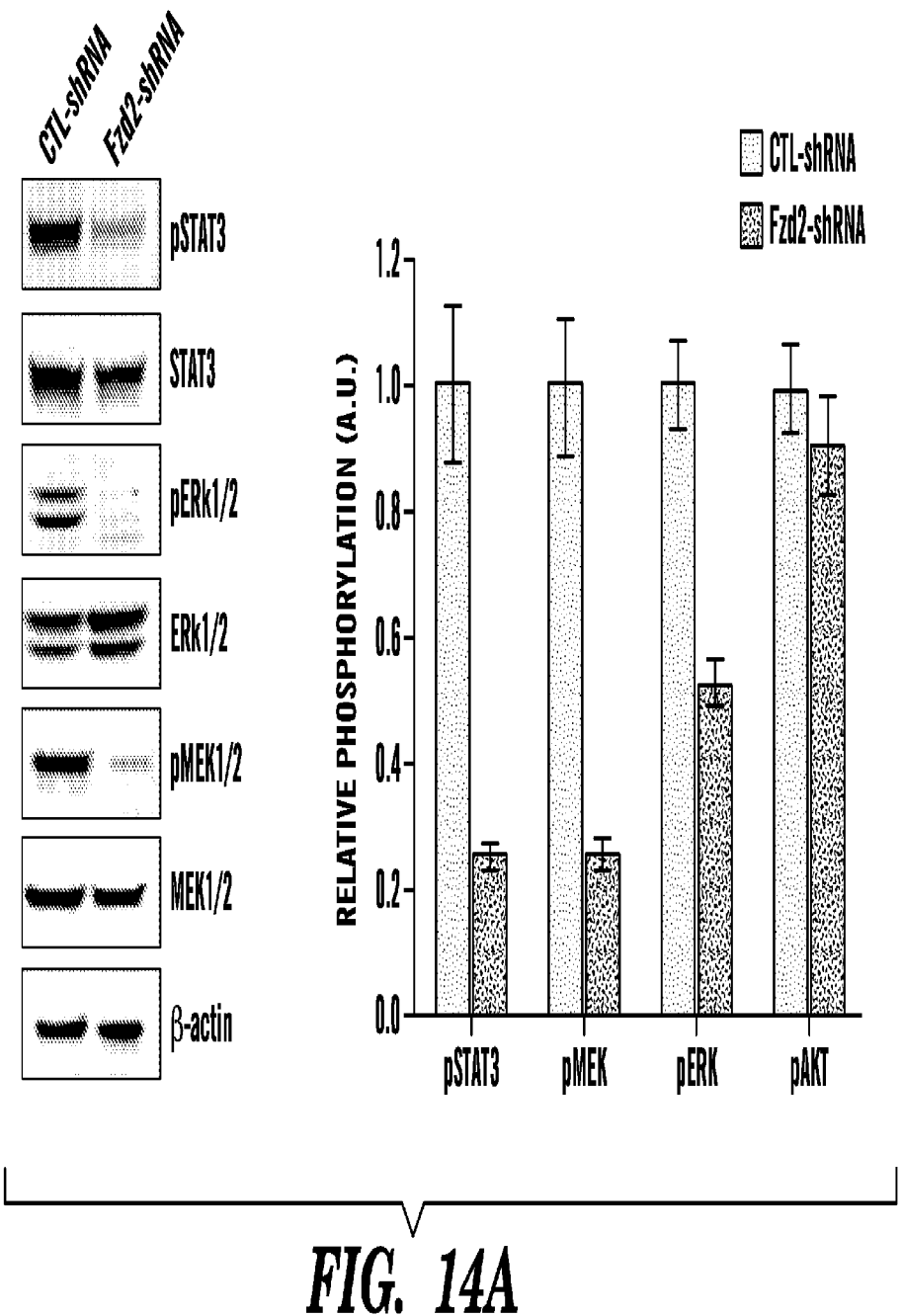
FIG. 14A-FIG. 14C shows experimental results that indicate Fzd2 regulates the phosphorylation status of Stat3, ERK1/2 and MEK1/2 as well as its transcription activity.
Figure 14B:
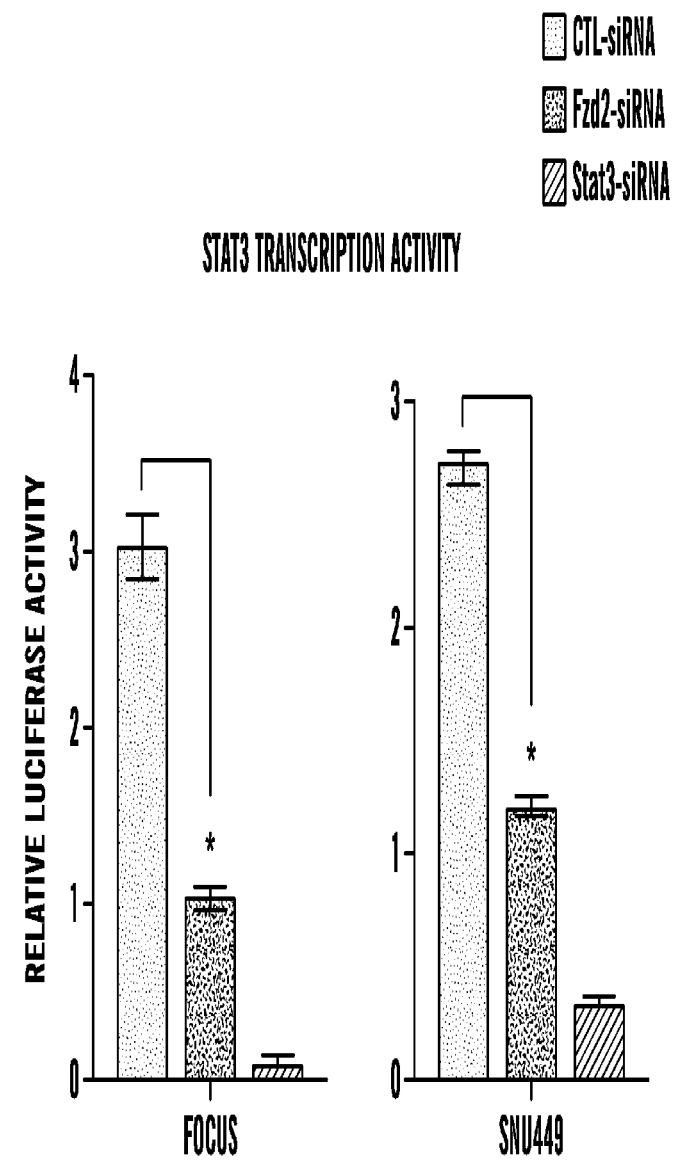
Figure 14C:
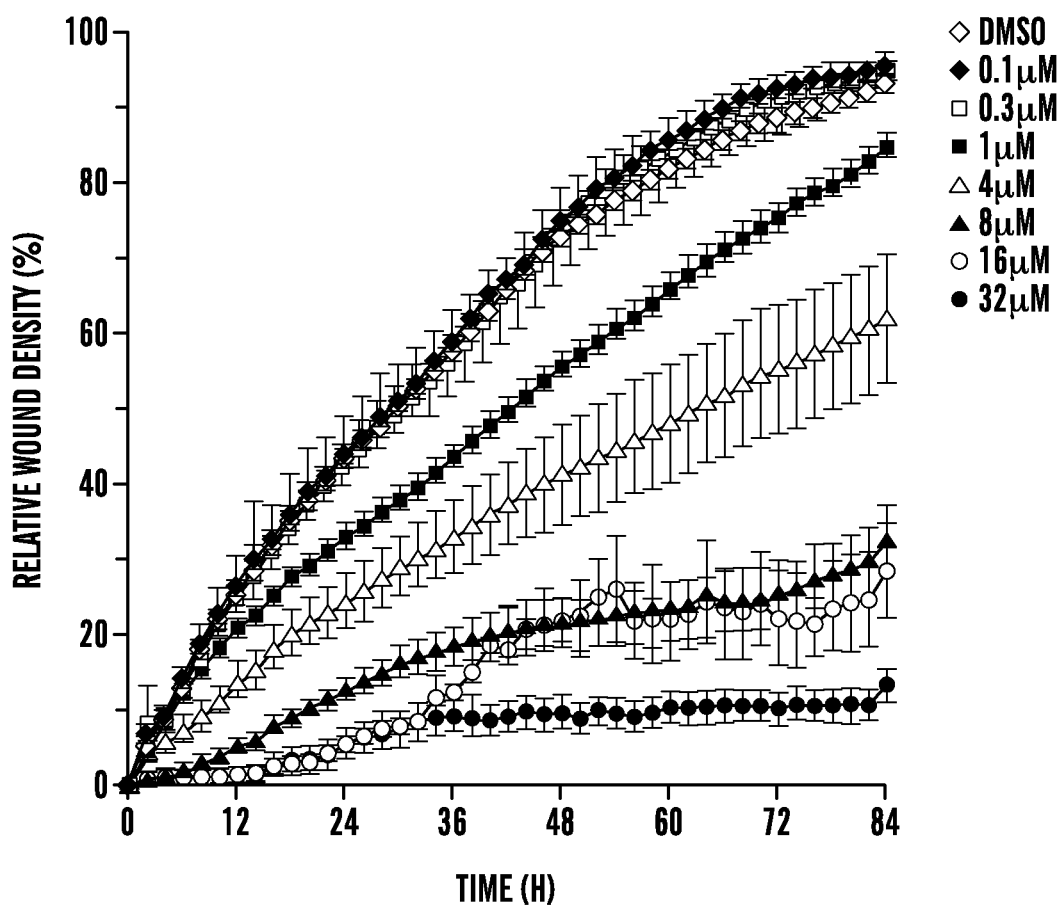

Analysis was performed to examine the phosphorylation of STAT3, ERK1/2, and MEK1/2 in wild-type FOCUS cells, and FOCUS cells with knockdown of Fzd2. Similar analysis was performed in other late stage cell lines and with treatment with anti-Fzd2 antibody. Results are shown in FIG. 14A. Stat3 transcription activity using a reporter/luciferase-based assay in wild-type FOCUS and SNU449 cells, and cells knockdown with Fzd2 or STAT3 is shown in FIG. 14A. Similar results were demonstrated in other late stage cell lines and with treatment with anti-Fzd2 antibody (FIG. 14C). The effect of small molecule inhibitor against Stat3 on cell migration of late stage HCC cell lines (FOCUS) is shown in FIG. 14C.

Figure 15C:
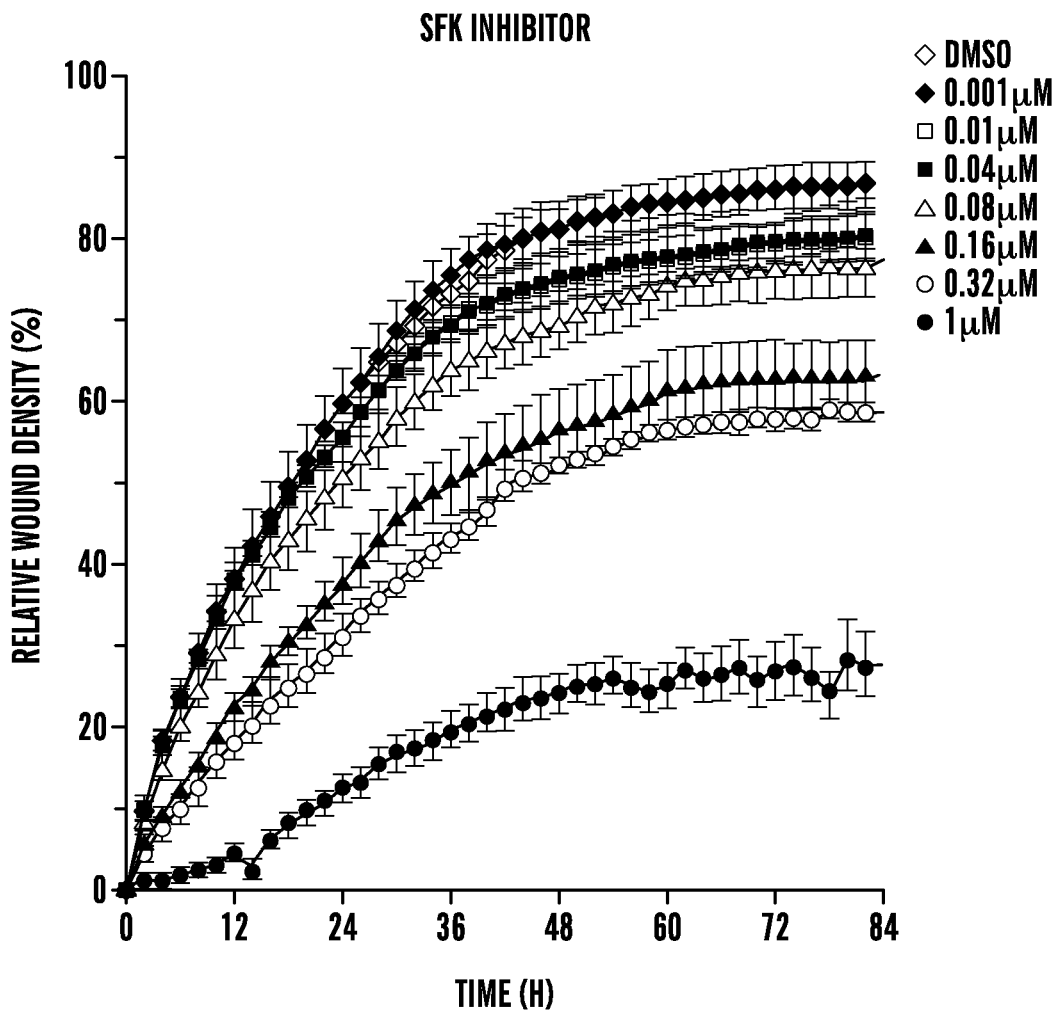

Fzd2 Regulates the Phosphorylation Status of Src Family Kinases which Phosphorylate Stat3 in Late Stage HCC Cell Lines Phosphorylation of src family kinases was analyzed in wild-type FOCUS cells, and FOCUS cells with knockdown of Fzd2 and in other late stage cell lines (FIG. 15A). The effect of inhibiting Src family kinase, with the small molecule inhibitor (dasatinib), was also examined. The inhibitor abolished stat3 phosphorylation in FOCUS cells (FIG. 15B). The effect of the inhibitor on cell migration of late stage HCC cell lines (FOCUS) was also investigated. Dose-response curves are shown in FIG. 15C.

What is claimed:

1. A method of treating cancer in a subject that exhibits overexpression of Fzd2 or overexpression of Wnt5a comprising administering to the subject a therapeutically effective amount of an antibody or antigen binding fragment thereof that specifically binds Fzd2 within a region corresponding to amino acids 125-163 and downmodulates Fzd2, such that the antibody or antigen binding fragment thereof is delivered to cancer cells of the subject, to thereby treat the cancer.

2. A method of inhibiting growth, migration and/or invasion of a cancer cell that exhibits overexpression of Fzd2 or overexpression of Wnt5a in a subject comprising administering to the subject a therapeutically effective amount of an antibody or antigen binding fragment thereof that specifically binds Fzd2 within a region corresponding to amino acids 125-163 and downmodulates Fzd2, such that the antibody or antigen binding fragment thereof is delivered to the cancer cells, to thereby treat the cancer.

3. The method of claim 2, wherein the antibody promotes internalization of Fzd2 by the cancer cells.

4. The method of claim 2, wherein the antibody prevents ligand binding to Fzd2.

5. The method of claim 2, wherein the antibody specifically binds to Fzd2 within a region of Fzd2 corresponding to amino acids 134-163 of Fzd2.

6. The method of claim 2, wherein the antibody specifically binds to Fzd2 within a region of Fzd2 corresponding to amino acids 144-163 of Fzd2.

7. The method of claim 2, wherein the antibody specifically binds to the epitope HGAEQICVGQNHSEDGAPAL (SEQ ID NO: 1).

8. The method of claim 2, wherein the antibody is monoclonal.

9. The method of claim 2, wherein the antibody is polyclonal.

10. The method of claim 2, wherein the antibody is humanized.

11. The method of claim 2, wherein the cancer is selected from the group consisting of gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer.

12. The method of claim 11, wherein the cancer is liver cancer.

13. The method of claim 12, wherein the cancer is late stage hepatocellular carcinoma.

14. The method of claim 1, wherein the antibody promotes internalization of Fzd2 by the cancer cells.

15. The method of claim 1, wherein the antibody prevents ligand binding to Fzd2.

16. The method of claim 1, wherein the antibody specifically binds to Fzd2 within a region of Fzd2 corresponding to amino acids 134-163 of Fzd2.

17. The method of claim 1, wherein the antibody specifically binds to Fzd2 within a region of Fzd2 corresponding to amino acids 144-163 of Fzd2.

18. The method of claim 1, wherein the antibody specifically binds to the epitope HGAEQICVGQNHSEDGAPAL (SEQ ID NO: 1).

19. The method of claim 1, wherein the antibody is monoclonal.

20. The method of claim 1, wherein the antibody is polyclonal.

21. The method of claim 1, wherein the antibody is humanized.

22. The method of claim 1, wherein the cancer is selected from the group consisting of gastrointestinal cancer, prostate cancer, ovarian cancer, breast cancer, head and neck cancer, lung cancer, non-small cell lung cancer, cancer of the nervous system, kidney cancer, retina cancer, skin cancer, liver cancer, pancreatic cancer, genital-urinary cancer and bladder cancer.

23. The method of claim 22, wherein the cancer is liver cancer.

24. The method of claim 23, wherein the cancer is late stage hepatocellular carcinoma.

* * * * *

SEQUENCE LISTING

```
<160> NUMBER OF SEQ ID NOS: 4

<210> SEQ ID NO 1
<211> LENGTH: 20
<212> TYPE: PRT
<213> ORGANISM: Homo sapiens

<400> SEQUENCE: 1

His Gly Ala Glu Gln Ile Cys Val Gly Gln Asn His Ser Glu Asp Gly
1               5                   10                  15

Ala Pro Ala Leu
            20

<210> SEQ ID NO 2
<211> LENGTH: 565
<212> TYPE: PRT
<213> ORGANISM: Homo sapiens

<400> SEQUENCE: 2

Met Arg Pro Arg Ser Ala Leu Pro Arg Leu Leu Leu Pro Leu Leu Leu
1               5                   10                  15

Leu Pro Ala Ala Gly Pro Ala Gln Phe His Gly Glu Lys Gly Ile Ser
            20                  25                  30
```

```
Ile Pro Asp His Gly Phe Cys Gln Pro Ile Ser Ile Pro Leu Cys Thr
         35                  40                  45

Asp Ile Ala Tyr Asn Gln Thr Ile Met Pro Asn Leu Leu Gly His Thr
 50                  55                  60

Asn Gln Glu Asp Ala Gly Leu Glu Val His Gln Phe Tyr Pro Leu Val
 65                  70                  75                  80

Lys Val Gln Cys Ser Pro Glu Leu Arg Phe Phe Leu Cys Ser Met Tyr
             85                  90                  95

Ala Pro Val Cys Thr Val Leu Glu Gln Ala Ile Pro Pro Cys Arg Ser
            100                 105                 110

Ile Cys Glu Arg Ala Arg Gln Gly Cys Glu Ala Leu Met Asn Lys Phe
        115                 120                 125

Gly Phe Gln Trp Pro Glu Arg Leu Arg Cys Glu His Phe Pro Arg His
        130                 135                 140

Gly Ala Glu Gln Ile Cys Val Gly Gln Asn His Ser Glu Asp Gly Ala
145                 150                 155                 160

Pro Ala Leu Leu Thr Thr Ala Pro Pro Gly Leu Gln Pro Gly Ala
                165                 170                 175

Gly Gly Thr Pro Gly Gly Pro Gly Gly Gly Ala Pro Pro Arg Tyr
            180                 185                 190

Ala Thr Leu Glu His Pro Phe His Cys Pro Arg Val Leu Lys Val Pro
        195                 200                 205

Ser Tyr Leu Ser Tyr Lys Phe Leu Gly Glu Arg Asp Cys Ala Ala Pro
    210                 215                 220

Cys Glu Pro Ala Arg Pro Asp Gly Ser Met Phe Phe Ser Gln Glu Glu
225                 230                 235                 240

Thr Arg Phe Ala Arg Leu Trp Ile Leu Thr Trp Ser Val Leu Cys Cys
                245                 250                 255

Ala Ser Thr Phe Phe Thr Val Thr Thr Tyr Leu Val Asp Met Gln Arg
                260                 265                 270

Phe Arg Tyr Pro Glu Arg Pro Ile Ile Phe Leu Ser Gly Cys Tyr Thr
        275                 280                 285

Met Val Ser Val Ala Tyr Ile Ala Gly Phe Val Leu Gln Glu Arg Val
    290                 295                 300

Val Cys Asn Glu Arg Phe Ser Glu Asp Gly Tyr Arg Thr Val Val Gln
305                 310                 315                 320

Gly Thr Lys Lys Glu Gly Cys Thr Ile Leu Phe Met Met Leu Tyr Phe
            325                 330                 335

Phe Ser Met Ala Ser Ser Ile Trp Trp Val Ile Leu Ser Leu Thr Trp
            340                 345                 350

Phe Leu Ala Ala Gly Met Lys Trp Gly His Glu Ala Ile Glu Ala Asn
            355                 360                 365

Ser Gln Tyr Phe His Leu Ala Ala Trp Ala Val Pro Ala Val Lys Thr
    370                 375                 380

Ile Thr Ile Leu Ala Met Gly Gln Ile Asp Gly Asp Leu Leu Ser Gly
385                 390                 395                 400

Val Cys Phe Val Gly Leu Asn Ser Leu Asp Pro Leu Arg Gly Phe Val
                405                 410                 415

Leu Ala Pro Leu Phe Val Tyr Leu Phe Ile Gly Thr Ser Phe Leu Leu
            420                 425                 430

Ala Gly Phe Val Ser Leu Phe Arg Ile Arg Thr Ile Met Lys His Asp
            435                 440                 445
```

```
Gly Thr Lys Thr Glu Lys Leu Glu Arg Leu Met Val Arg Ile Gly Val
    450                 455                 460

Phe Ser Val Leu Tyr Thr Val Pro Ala Thr Ile Val Ile Ala Cys Tyr
465                 470                 475                 480

Phe Tyr Glu Gln Ala Phe Arg Glu His Trp Glu Arg Ser Trp Val Ser
            485                 490                 495

Gln His Cys Lys Ser Leu Ala Ile Pro Cys Pro Ala His Tyr Thr Pro
                500                 505                 510

Arg Met Ser Pro Asp Phe Thr Val Tyr Met Ile Lys Tyr Leu Met Thr
            515                 520                 525

Leu Ile Val Gly Ile Thr Ser Gly Phe Trp Ile Trp Ser Gly Lys Thr
        530                 535                 540

Leu His Ser Trp Arg Lys Phe Tyr Thr Arg Leu Thr Asn Ser Arg His
545                 550                 555                 560

Gly Glu Thr Thr Val
                565

<210> SEQ ID NO 3
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Gly Gly Cys
1               5

<210> SEQ ID NO 4
<211> LENGTH: 30
<212> TYPE: PRT
<213> ORGANISM: Homo sapiens

<400> SEQUENCE: 4

Glu Arg Leu Arg Cys Glu His Phe Pro Arg His Gly Ala Glu Gln Ile
1               5                   10                  15

Cys Val Gly Gln Asn His Ser Glu Asp Gly Ala Pro Ala Leu
            20                  25                  30
```